(12) United States Patent
Brake et al.

(10) Patent No.: US 11,346,650 B2
(45) Date of Patent: May 31, 2022

(54) INTERFEROMETRIC SPECKLE VISIBILITY SPECTROSCOPY

(71) Applicant: California Institute of Technology, Pasadena, CA (US)

(72) Inventors: Joshua Brake, Pasadena, CA (US); Jian Xu, Pasadena, CA (US); Changhuei Yang, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/946,063

(22) Filed: Jun. 4, 2020

(65) Prior Publication Data

US 2020/0386535 A1 Dec. 10, 2020

Related U.S. Application Data

(60) Provisional application No. 62/856,963, filed on Jun. 4, 2019.

(51) Int. Cl.
   *G01B 9/02* (2022.01)
   *G01B 11/24* (2006.01)
   *G01B 9/02055* (2022.01)
   *G01B 9/02015* (2022.01)

(52) U.S. Cl.
   CPC ..... *G01B 9/02082* (2013.01); *G01B 9/02024* (2013.01); *G01B 11/2441* (2013.01)

(58) Field of Classification Search
   CPC ............ G01B 9/02024; G01B 9/02082; G01B 11/2441; G01N 21/453; G01N 21/47; G01N 2021/1789; G01N 2021/1795; G01N 2021/479; G01N 2021/4792; G03H 2001/0445
   See application file for complete search history.

(56) References Cited

U.S. PATENT DOCUMENTS

| | | | |
|---|---|---|---|
| 2012/0095354 A1* | 4/2012 | Dunn | A61B 5/0261 600/504 |
| 2012/0301967 A1* | 11/2012 | Nadkarni | G01N 33/4905 436/69 |

(Continued)

FOREIGN PATENT DOCUMENTS

| | | |
|---|---|---|
| KR | 10-2001-0051917 | 6/2001 |
| KR | 10-2017-0057827 | 5/2017 |

OTHER PUBLICATIONS

Ancellet, Gerard M. and Menzies, Robert T., "Atmospheric correlationtime measurements and effects on coherent Doppler lidar," JOSA A, (Feb. 1, 1987), 4(2):367-373.

(Continued)

*Primary Examiner* — Michael A Lyons
(74) *Attorney, Agent, or Firm* — Sheila Martinez-Lemke; Weaver Austin Villeneuve & Sampson LLP

(57) ABSTRACT

Interferometric speckle visibility spectroscopy methods, systems, and non-transitory computer readable media for recovering sample speckle field data or a speckle field pattern from an off-axis interferogram recorded by one or more sensors over an exposure time and determining sample dynamics of a sample being analyzed from speckle statistics of the speckle field data or the speckle field pattern.

25 Claims, 29 Drawing Sheets

(56) References Cited

U.S. PATENT DOCUMENTS

| | | | | |
|---|---|---|---|---|
| 2012/0307035 | A1* | 12/2012 | Yaqoob | G01B 9/02084 348/79 |
| 2013/0088568 | A1* | 4/2013 | Nolte | G01N 21/27 348/40 |
| 2013/0096017 | A1* | 4/2013 | Nolte | G03H 1/0443 506/8 |
| 2019/0313912 | A1* | 10/2019 | Alford | A61B 5/4064 |
| 2019/0336005 | A1* | 11/2019 | Alford | A61B 5/0066 |
| 2019/0336007 | A1* | 11/2019 | Ruan | A61B 5/4064 |
| 2020/0182788 | A1* | 6/2020 | Shaked | G03H 1/0005 |
| 2020/0333245 | A1* | 10/2020 | Mohseni | A61B 5/0066 |

OTHER PUBLICATIONS

Bandyopadhyay, R., et al., "Speckle-visibility spectroscopy: A tool to study time-varying dynamics," Rev. Sci. Instrum., (Jun. 3, 2005), 76.

Beak, YoonSeok et al., "Kramers-Kronig holographic imaging for high-space-bandwidth product," Optica, (Jan. 7, 2019), 6(1):45-51.

Boas, D. A. and Dunn, A. K., "Laser speckle contrast imaging in biomedical optics," Journal of Biomedical Optics, (Jan./Feb. 2010), vol. 15, No. 1, p. 011109, 12 pages.

Boas, D. A., et al., "Scattering and imaging with diffusing temporal field correlations," Physical Review Letters, (Aug. 28, 1995), vol. 75, No. 9, pp. 1855-1858.

Cheung, C., et al., "In vivo cerebrovascular measurement combining diffuse near-infrared absorption and correlation spectroscopies," Phys. Med. Biol. (Jul. 6, 2001), 46, 2053-2065.

Dirnagl, U., et al., "Coupling of cerebral blood flow to neuronal activation: Role of adenosine and nitric oxide," Am. J. Physiol.-Hear. Circ. Physiol., (Jul. 1, 1994), 267(1):H296-301.

Dunn, A. K., "Laser speckle contrast imaging of cerebral blood flow," Ann. Biomed. Eng., (Feb. 2012), 40, 367-377.

Dunn, A. K., et al., "Dynamic imaging of cerebral blood flow using laser speckle," J. Cereb. Blood Flow Metab., (Mar. 1, 2001), 21, 195-201.

Durduran, T., et al., "Diffuse optics for tissue monitoring and tomography," Reports Prog. Phys., (Jul. 2010), 73(7): 076701.

Goodman, J. W., "Some fundamental properties of speckle," JOSA, (Nov. 1, 1976), vol. 66, No. 11, pp. 1145-1150.

Huppert, T. J., et al., "HomER: A review of time-series analysis methods for near-infrared spectroscopy of the brain," Appl. Opt., (Apr. 1, 2009), 48.

Lou, H. C., et al., "The concept of coupling blood flow to brain function," Ann. Neurol., (Sep. 1987), 22(3):289-297.

Pine, D., et al., "Diffusing-wave spectroscopy: Dynamic light scattering in the multiple scattering limit," Journal de Physique, (Sep. 15, 1990), vol. 51, No. 18, pp. 2101-2127.

Selb, J., et al., "Sensitivity of near-infrared spectroscopy and diffuse correlation spectroscopy to brain hemodynamics: simulations and experimental findings during hypercapnia," Neurophotonics., (Jul.-Sep. 2014), 1(1):015005.

Valdes, C. P., et al., "Speckle contrast optical spectroscopy, a non-invasive, diffuse optical method for measuring microvascular blood flow in tissue," Biomed. Opt. Express., (Jul. 23, 2014), 5, 2769-2784.

Wang, D. et al., "Fast blood flow monitoring in deep tissues with real-time software correlators", Biomed. Opt. Express., (Dec. 14, 2016), 7, 776-797.

Zhao, M., et al., "Noncontact Speckle Contrast Diffuse Correlation Tomography of Blood Flow Distributions in Burn Wounds: A Preliminary Study", Military Medicine, (Jan. 7, 2020), 185(Supplement_1):82-7.

Zhou, Wenjun, et al., "Highly parallel, interferometric diffusing wave spectroscopy for monitoring cerebral blood flow dynamics," Optica 5, 518-527 (May 2018).

U.S. Appl. No. 62/856,963, filed Jun. 4, 2019, Brake et al.

International Search Report dated Sep. 15, 2020 for International Patent Application No. PCT/US20/036146.

Written Opinion of the International Searching Authority dated dated Sep. 15, 2020 for International Patent Application No. PCT/US20/036146.

Xu J, Jahromi AK, Brake J, Robinson JE, Yang C. Interferometric speckle visibility spectroscopy (ISVS) for human cerebral blood flow monitoring. APL Photonics. Dec. 1, 2020;5(12): 126102.

International Preliminary Report on Patentability dated Dec. 16, 2021 for International Patent Application No. PCT/US20/036146.

* cited by examiner

INTERFEROMETRIC SPECKLE VISIBILITY SPECTROSCOPY

CROSS-REFERENCES TO RELATED APPLICATIONS

This application claims priority to and benefit of U.S. Provisional Patent Application No. 62/856,963, titled "Interferometric Speckle Visibility Spectroscopy" and filed on Jun. 4, 2019, which is hereby incorporated by reference in its entirety and for all purposes.

FIELD

Certain embodiments pertain to interferometric speckle visibility spectroscopy systems and methods that can be implemented in, for example, biomedical measurements and atmospheric measurements.

BACKGROUND

High-fidelity measurement of functional and structural information inside biological tissue is critical in many fields of biomedicine. Light offers advantages in biological imaging since it can be safely used, can measure biological information at the cellular scale, and can support high temporal resolutions. However, light-based imaging methods have been stymied by the optical opacity of biological tissue due to its refractive index heterogeneity, which can prevent imaging deeply within the tissue. Methods such as optical wavefront shaping have been able to reclaim scattered light and peer deeper into tissue for high-resolution imaging and excitation, but these methods require complicated optical setups.

SUMMARY

Certain aspects pertain to methods for interferometric speckle visibility spectroscopy. These methods include (i) recovering sample speckle field data or a speckle field pattern from an off-axis interferogram recorded by one or more sensors over an exposure time; and (ii) determining sample dynamics of a sample being analyzed from speckle statistics of the speckle field data or the speckle field pattern. In one implementation, the sample dynamics comprise a decorrelation time and/or a movement of an object in the sample. In some cases, the sample speckle field data is recovered by Fourier transforming the off-axis interferogram to generate data in spatial frequency space comprising at least one off-axis lobe and using a spatial frequency filter to crop the sample speckle field data from the at least one off-axis lobe.

Certain aspects pertain to non-transitory computer readable media for interferometric speckle visibility spectroscopy. The non-transitory computer readable media comprises program instructions, wherein the program instructions, when executed by one or more processors, are configured to cause the one or more processors to (i) recover sample speckle field data or a speckle field pattern from an off-axis interferogram recorded by one or more sensors over an exposure time and (ii) determine sample dynamics of a sample being analyzed from speckle statistics of the speckle field data or the speckle field pattern. In one implementation, the sample dynamics comprise a decorrelation time and/or a movement of an object in the sample. In some cases, the sample speckle field data is recovered by Fourier transforming the off-axis interferogram to generate data in spatial frequency space comprising at least one off-axis lobe and using a spatial frequency filter to crop the sample speckle field data from the at least one off-axis lobe.

Certain aspects pertain to interferometric speckle visibility spectroscopy systems. These systems includes one or more optical systems configured to interfere an off-axis reference beam with a sample signal at one or more sensors and one or more processors configured to execute instructions to cause the one or more processors to (i) recover sample speckle field data or a speckle field pattern from an off-axis interferogram recorded by one or more sensors over an exposure time and (ii) determine sample dynamics of a sample being analyzed from speckle statistics of the speckle field data or the speckle field pattern.

These and other features are described in more detail below with reference to the associated drawings.

BRIEF DESCRIPTION OF THE DRAWINGS

FIG. 13A is a graph with a plot of effective speckle visibility over time (seconds) for a dorsal skin flap as measured by an iSVS system in transmission mode where the laser power was 1 mW, according to one example.

FIG. 14A is a graph with a plot of effective speckle visibility over time (seconds) for a dorsal skin flap as measured by an iSVS system in transmission mode where the laser power was 0.5 mW, according to one example.

FIG. 15A is a graph with a plot of effective speckle visibility over time (seconds) for a dorsal skin flap as measured by an iSVS system in transmission mode where the laser power was 0.26 mW, according to one example.

FIG. 16A is a graph with a plot of effective speckle visibility over time (seconds) for a dorsal skin flap as measured by an iSVS system in transmission mode where the laser power was 0.13 mW, according to one example.

FIG. 17A is a graph with a plot of effective speckle visibility over time (seconds) for a dorsal skin flap as measured by an iSVS system in transmission mode where the laser power was 0.06 mW, according to one example.

FIG. 18A is a graph with a plot of effective speckle visibility over time (seconds) for a dorsal skin flap as measured by an iSVS system in transmission mode where the laser power was 0.03 mW, according to one example.

DETAILED DESCRIPTION

Figure 1A:
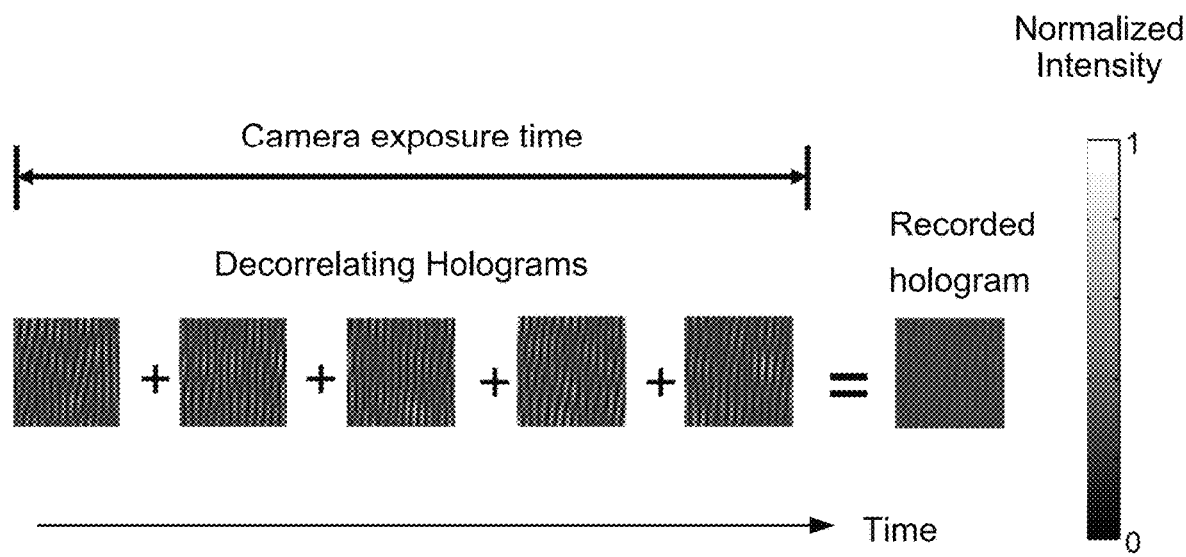
FIG. 1A depicts five (5) speckle patterns measured by an interferometric speckle visibility spectroscopy (iSVS) system at times $t_1$-$t_5$ where the scattering medium is static, according to embodiments.

Different aspects are described below with reference to the accompanying drawings. The features illustrated in the drawings may not be to scale. In the following description, numerous specific details are set forth in order to provide a thorough understanding of the presented embodiments. The disclosed embodiments may be practiced without one or more of these specific details. In other instances, well-known operations have not been described in detail to avoid unnecessarily obscuring the disclosed embodiments. While the disclosed embodiments will be described in conjunction with the specific embodiments, it will be understood that it is not intended to limit the disclosed embodiments. Moreover, although many disclosed embodiments of interferometric speckle visibility spectroscopy (iSVS) methods and systems will be described for biomedical applications such as used in determining the dynamics of blood flow, it would be understood that these embodiments are not so limited. The iSVS methods and systems disclosed herein can also have applications in other areas such as, for example, determining dynamics of atmospheric measurements.

I. Introduction

Sample Dynamics

When coherent light illuminates a dynamic scattering sample such as living tissue, the interference of the different scattered light components generates an optical interference pattern called a speckle field. When the scatterers within the sample move, this generates temporal fluctuations in the speckle pattern. These changes in the speckle pattern are related to the movement of scatterers (i.e., scattering objects) within the sample.

Generally speaking, there are two main techniques to calculate the movement speed of an object and other sample dynamics. Here sample dynamics refers to the movement of an element or elements within a sample. For example, in the context of biological imaging, particles such as red blood cells may be circulating and impart changes to the optical transmission of light through the sample over time. Other types of sample dynamics may include, for example, the movement of a vehicle or person within an optically scattering medium such as a fog or cloud. One technique is to use a high-speed sensor (such as a single pixel detector like a single photon counting module or avalanche photodetector or a high-speed array detector such as a CMOS or 2D single photon avalanche diode) to capture multiple measurements and directly calculate the correlation between subsequent frames at times $t_i$ to calculate movement speed of the scattering object. This technique generally requires a high-speed device with a frame rate capable of capturing multiple frames within a single decorrelation time. An example of this first technique is diffusing wave spectroscopy (DWS), which is discussed in Pine, D., Weitz, D., Zhu, J., and Herbolzheimer, E., "Diffusing-wave spectroscopy: Dynamic light scattering in the multiple scattering limit," *Journal de Physique*, vol. 51, no. 18, pp. 2101-2127, 1990, which is hereby incorporated by reference in its entirety. The application of the DWS technique to biological tissue, e.g., to measure blood flow speed, is diffuse correlation spectroscopy (DCS), which is discussed in Boas, D. A., Campbell, L., and Yodh, A. G., "Scattering and imaging with diffusing temporal field correlations," *Physical Review Letters*, vol. 75, no. 9, pp. 1855-1858 (1995), which is hereby incorporated by reference in its entirety. Examples of DCS systems can be found in Cheung, C., Culver, J. P., Takahashi, K., Greenberg, J. H., Yodh, A. G., "In vivo cerebrovascular measurement combining diffuse near-infrared absorption and correlation spectroscopies," *Phys. Med. Biol.* 46,2053-2065 (2001) and Huppert, T. J., Diamond, S. G., Franceschini, M. A., Boas, D. A., "HomER: A review of time-series analysis methods for near-infrared spectroscopy of the brain," *Appl. Opt.* 48 (2009), which are hereby incorporated by reference in their entireties. In one example of a DCS system, a sensitive single-pixel photodetector, such as an avalanche photodiode, is used to collect light from a single speckle grain of the speckle pattern and monitor its fluctuations over time. Then, by computing the temporal autocorrelation function of the intensity time trace, $g_2(t)$, the decay can be fit to a theoretical model to extract quantities of interest such as the diffusion coefficient of the sample under test. One of the limitations of this DCS system is that it can only sample light from a single speckle grain or a few speckle grains in order to maximize contrast and signal-to-noise ratio (SNR) in the measurement, which fundamentally limits throughput of the measurement. The performance of this DCS system is ultimately constrained by the total collected photon budget required for a reasonable SNR. Since this DCS system exploits only one or a few speckles grains from the scattered light, in order to get a sufficient number of signal photons for a relatively accurate measure of the sample flow dynamics, the required measurement time of the detector for one data point (e.g. one measurement of cerebral blood flow (CBF)) is typically no less than tens of milliseconds. There is therefore a tradeoff between the measurement time and the sensitivity of the system: a high SNR measurement requires a relatively long measurement time, which results in a relatively low sampling rate.

Another technique for calculating the movement speed of a scattering object is to infer the speed from the blurring of the object within an image frame recorded during a single exposure time, T. The amount of blurring can be used to quantitatively determine how fast the sample is decorrelating (i.e., the decorrelation time). By using the blurring inference based on a single exposure time to measure decorrelation time instead of direct calculation from multiple frames, it is no longer necessary to capture multiple frames within a single decorrelation time, which relaxes requirement for a high frame rate. As used herein, a "decorrelation time" refers to the point when the temporal autocorrelation function $g_1(t)$ drops below a certain threshold. Depending on the specific form of $g_1(t)$, some common choices for this threshold are $1/e$ or $1/e^2$. The decorrelation time is calculated by computing the temporal autocorrelation function using the measured data and then extracting the point at which the function drops below the threshold from a theoretical model fitted to the data. The movement speed can also be determined from the parameters of the fitted model which take into account the impact of the sample dynamics on the autocorrelation function.

An example of a technique that uses the blurring inference to be able to calculate decorrelation time is speckle visibility spectroscopy (SVS). Conventional SVS measures the decorrelation time from a single frame using statistics of the blurred speckle patterns captured during a single exposure time longer than the decorrelation time. One example of a conventional SVS system uses a camera with a detector array, such as a charge-coupled device (CCD) camera, to capture a two-dimensional speckle pattern containing many speckle grains, and uses the statistics determined from the blurred speckle pattern to calculate the speckle decorrelation time. For a given camera integration (exposure) time that is longer than the speckle decorrelation time, different speckle decorrelation times result in speckle pattern frames with different extents of blurring. Examples of conventional SVS systems can be found in Dunn, A. K., Bolay, H., Moskowitz, M. A., Boas, D. A., "Dynamic imaging of cerebral blood flow using laser speckle," *J. Cereb. Blood Flow Metab.* 21, 195-201 (2001), Bandyopadhyay, R., Gittings, A. S. Suh, S. S. Dixon, P. K., Durian, D. J., "Speckle-visibility spectroscopy: A tool to study time-varying dynamics," *Rev. Sci. Instrum.* 76 (2005), Dunn, A. K., "Laser speckle contrast imaging of cerebral blood flow," *Ann. Biomed. Eng.* 40, 367-377 (2012), Valdes, C. P., Varma, H. M., Kristoffersen, A. K., Dragojevic, T., Culver, J. P., Durduran, T., "Speckle contrast optical spectroscopy, a non-invasive, diffuse optical method for measuring microvascular blood flow in tissue," *Biomed. Opt. Express.* 5, 2769 (2014), and Zhao, M., Mazdeyasna, S., Huang, C., Agochukwu-Nwubah, N., Bonaroti, A., Wong, L., Yu, G., "Noncontact Speckle Contrast Diffuse Correlation Tomography of Blood Flow Distributions in Burn Wounds: A Preliminary Study," *Military Medicine*, vol. 185, pp. 82-87 (2020), which are hereby incorporated by reference in their entireties.

Conventional SVS systems use a camera to record the intensity distribution of dynamic speckle fields which are then used to characterize the speckle field decorrelation time r. If the camera exposure time T is longer than the speckle field decorrelation time r, there will be multiple independent speckle fields recorded by the camera within the exposure time. Since these independent speckle fields arrive at the camera at different times, the speckle pattern recorded over the entire exposure is the intensity summation of these independent speckle patterns. If the speckle pattern does not decorrelate (e.g., when the sample is static), then the intensity summation over the exposure time simply records a scaled version of a stable speckle pattern. However, if the speckle changes during the exposure time, the independent speckle patterns will add incoherently and ultimately modify the statistics of the recorded speckle pattern.

One statistic of interest in a speckle pattern is speckle contrast ($\kappa$), defined as:

$$\kappa = \frac{\sigma}{\mu}, \quad \text{(Eqn. 1)}$$

where $\sigma$ the standard deviation of the recorded speckle pattern and $\mu$ is the mean intensity of the recorded speckle pattern.

Speckle contrast decreases as multiple independent speckle intensity patterns add up on the camera, and mathematical models have been developed which relate the measured speckle pattern contrast to the camera exposure time T and the speckle field decorrelation time $\tau$ as discussed in Boas, D. A. and Dunn, A. K., "Laser speckle contrast imaging in biomedical optics," *Journal of Biomedical Optics*, vol. 15, no. 1, p. 011 109 (2010), which is hereby incorporated by reference in its entirety. Exploiting this relationship, the speckle field decorrelation time can be calculated by measuring the speckle pattern contrast and inferring information about the activities that influenced the dynamic properties of the scattering sample.

There are, however, two conditions that must be satisfied when using conventional SVS to take measurements that can be used to accurately calculate dynamic properties: (1) the Siegert relation should hold ("Condition 1"), and (2) the photon number should be large enough to overwhelm the camera noise ("Condition 2"). For Condition 1, the Siegert relation assumes a fully-developed speckle pattern and then takes advantage of its statistical properties to convert the intensity autocorrelation function $g_2(t)$ to the complex field autocorrelation function $g_1(t)$. If the speckles are not fully developed, which can happen if the photons do not experience multiple scattering events in the scattering medium, the output speckle pattern no longer follows fully-developed speckle statistics as discussed in "Some fundamental properties of speckle," *JOSA*, vol. 66, no. 11, pp. 1145-1150 (1976), which is hereby incorporated by reference in its entirety. In this case, the Siegert relation does not hold and there is no direct connection between $g_2(t)$ and $g_1(t)$. Moreover, there is an empirical factor $\beta$ when converting $g_2(t)$ to $g_1(t)$, which also introduces systematic inaccuracy to the measurement. For Condition 2, if the speckle field decorrelation time changes quickly, the camera should have a short exposure time and high frame rate to monitor the change of the decorrelation time, which limits the number of available signal photons in each frame. In this case, the dark current and readout noise of the camera can swamp the sample signal. Thus, conventional SVS takes measurements that suffer from camera noise, which limits the sensitivity of SVS techniques. Moreover, when using conventional SVS to detect photons delivered into samples at depths, e.g., greater than 1 cm, the amount of reflected photons reaching the detector array may be less than 1 photon/pixel within an exposure time. In these cases, camera noise may overwhelm the weak signal from detected deep photons.

II. Interferometric Speckle Visibility Spectroscopy (iSVS)

Certain aspects pertaining to interferometric speckle visibility spectroscopy (iSVS) systems and methods circumvent the two conditions discussed in Section I above, and thus, can determine $g_1(t)$ directly without needing to use $g_2(t)$ and $\beta$. These iSVS systems and/or methods implement an interferometric optical arrangement (e.g., off-axis holography) to boost the sample signal to overcome camera noise. For example, an iSVS system and/or method of one implementation can boost the signal to achieve a suitable signal-to-noise ratio (SNR) when the mean pixel value from the sample signal is less than 1. In one aspect, iSVS systems and/or methods described herein use interferometric measurements of the electrical field magnitude of a single frame (i.e., interferogram) recorded during a single exposure time to calculate a decorrelation time of the sample. The iSVS systems and/or methods infer sample dynamics from the speckle statistics measured in a single frame speckle pattern recorded. Certain iSVS systems and/or methods described herein enable high-speed and sensitive measurement of the optical field dynamics with shot-noise limited sensitivity.

When a scattering medium is static, the electric field remains constant through all the time stamps during a single decorrelation time. This results in an overall integrated electric field which is a scaled version of the static speckle pattern. However, when the sample is decorrelating, the electric field changes as a function of time. This generates a speckle pattern with a lower average amplitude, since the resultant electric field phasor at each point within the frame is an average of a series of phasors with random amplitudes and phases. Therefore, the average value of the speckle electric field can be used to quantitatively measure the decorrelation time of the sample.

In certain implementations, the exposure time of the one or more sensors of the camera is set to at least one order of magnitude longer than the decorrelation time. In one example, the exposure time of the one or more sensors of the camera is set as one order of magnitude longer than the decorrelation time, i.e., 10 times longer.

The decorrelation time used to calculate the exposure time can be estimated from D. Wang, A. B. Parthasarathy, W. B. Baker, K. Gannon, V. Kavuri, T. Ko, S. Schenkel, Z. Li, Z. Li, M. T. Mullen, J. A. Detre, A. G. Yodh, Fast blood flow monitoring in deep tissues with real-time software correlators. *Biomed. Opt. Express.* 7, 776 (2016), which is hereby incorporated by reference in its entirety. Alternatively, the decorrelation time used to determine the exposure time can be determined using a conventional DCS method. Once the decorrelation time is estimated, the exposure time can be set accordingly and more accurate measurements can be taken by the iSVS system.

According to certain aspects, iSVS systems include an off-axis interferometric optical arrangement that implements a tilted reference beam (e.g., a plane wave reference beam tilted an oblique angle θ) to interfere with the sample signal at the one or more sensors of the camera, and the camera records one or more off-axis holograms (also referred to herein as "off-axis interferograms"). Each off-axis hologram recorded by the camera is a measurement of the intensity of the interference pattern integrated over a single exposure time. The recorded data from an off-axis hologram can be used in single-shot complex sample field reconstruction. The off-axis interferometric arrangement removes the constraint of condition 1 since the complex sample field can be retrieved from the off-axis holograms and the $g_1(t)$ can be calculated directly. Also, the reference beam enables the low signal field to be boosted above the camera noise threshold using the heterodyne gain of the reference beam, and thus, the constraints of condition 2 become less restrictive or no longer restrictive.

According to certain aspects, an iSVS system and/or method implements a tilted planar reference beam for off-axis hologram acquisition. In these aspects, the tilted planar reference beam, $E_r(r, t) = E_0(r)\exp(ik \cdot r)$, and the sample beam, $E_s(r, t) = E_s(r)\exp(i\phi_s(r, t))$, interfere on the camera, where $r = (x, y)$ is the spatial coordinate, t is the time, $E_0$ is the amplitude of the reference beam, k is the wave vector corresponding to the tilted plane wave reference beam, and $E_s(r, t)$ and $\phi_s(r, t)$ are the amplitude and phase of the signal light field, respectively. The camera can record over an exposure time an intensity speckle pattern I(r) at position $r = (x, y)$ due to the interference of the sample and the reference beam given by:

$$I(r) = \int_0^T |E_r(r, t) + E_s(r, t)|^2 dt \quad \text{(Eqn. 2)}$$
$$= \int_0^T |E_r(r, t)|^2 + |E_s(r, t)|^2 +$$
$$2E_r(r, t)E_s(r, t) \cos(k \cdot r - \phi_s(r, t))dt$$

where t=0 defines the beginning of the exposure and T is the exposure time. Since the reference beam is tilted at a tilt angle θ with respect to the sample beam for off-axis holography, this generates an interference fringe pattern that separates the third term in Eqn. 2 in the spatial frequency domain from the other data. Therefore, by taking the Fourier transform of the captured off-axis hologram I(r) in Eqn. 2, and using the known planar reference beam field profile, the complex sample field can be recovered by spatially filtering the image in the spatial frequency domain as discussed below.

In certain implementations, the iSVS systems and/or methods are configured to take the Fourier transform of an off-axis interferogram which results in data having three distinct lobes as described below with reference to an example shown in FIG. 2. The data from the central lobe corresponds to the Fourier transform of the combined first two terms (DC terms) in Eqn. 2. The data from the two side lobes corresponds to the Fourier transform of the third term in Eqn. 2. According to certain implementations, iSVS systems and/or methods isolate the data from at least one of the two side lobes in the spatial frequency domain to extract the complex sample field $E_s(r, t)$. Since these two lobes contain the same information and are simply complex conjugates of each other (commonly referred to as twin images in off-axis holography), either lobe may be used to extract the sample dynamics. After extracting the complex sample field $E_s(r, t)$ from the off-axis interferogram, speckle statistics of this sample speckle field can be further analyzed to retrieve the dynamics of the scattering sample (sample dynamics). It should be noted that the two side lobes in Fourier plane are phase conjugate pairs, therefore extracting one of the pairs is sufficient for reconstructing the sample field. The sample dynamics are directly linked to the average amplitude of the sample speckle field. If the sample is static, then the overall amplitude of the sample speckle field is at its maximum. If the sample is decorrelating, the overall average amplitude of the sample speckle field decreases. The degree to which it decreases provides a quantitative measure of the decorrelation time.

Figure 1B:
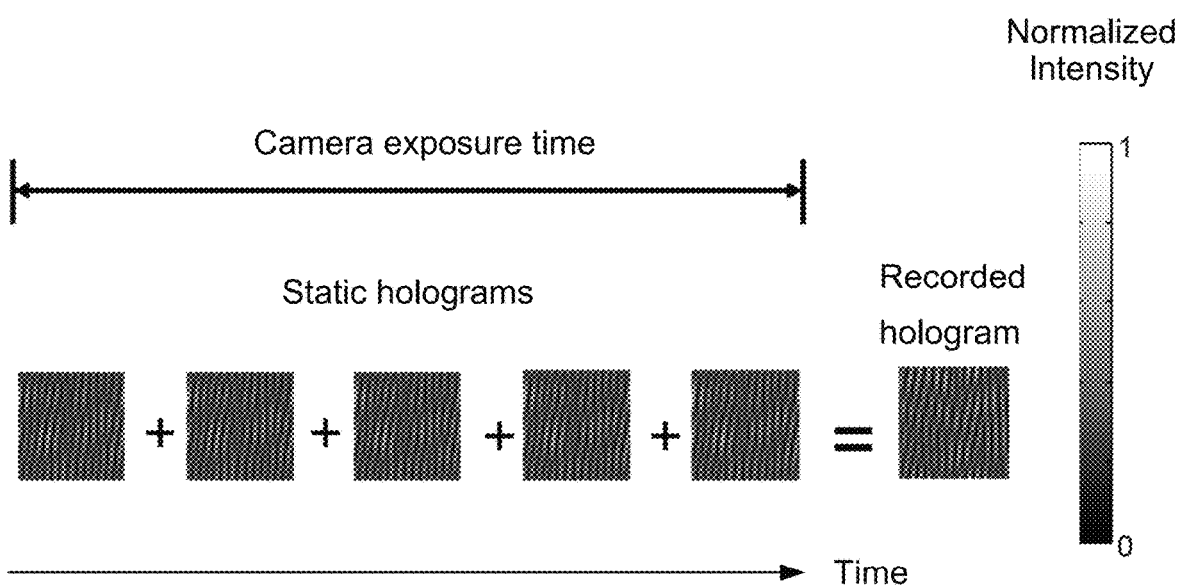
FIG. 1B depicts five (5) speckle patterns measured by an interferometric speckle visibility spectroscopy (iSVS) system at times $t_1$-$t_5$ where the scattering medium is decorrelating, according to embodiments.

FIGS. 1A and 1B is an illustration for the purpose of depicting the difference between the static and decorrelating samples in iSVS measurements (e.g., intensity measurements) recorded over an exposure time that are integrated to generate a recorded hologram. FIG. 1A includes five (5) iSVS measurements of the sample speckle field take at times $t_1$-$t_5$ during an exposure time where the scattering medium is static. At each time $t_1$-$t_5$, the sample speckle field is the same during the iSVS measurements in FIG. 1A. FIG. 1B includes five (5) iSVS measurements of the sample speckle field take at times $t_1$-$t_5$ where the scattering medium is decorrelating. In this example, the scattering medium is decorrelating and the measurements of the sample speckle pattern at the time stamps $t_1$-$t_5$ taken over the exposure time are different.

As illustrated in FIG. 1A, if the sample speckle field is static, then the amplitude and phase of a specific coherence area (i.e., a speckle grain) is fixed as a function of time. Thus, the integration of the static sample field over the exposure time in the recorded hologram will simply create a scaled version of the measured static speckle pattern.

On the other hand, if the sample speckle field is decorrelating due to motion within the scattering medium as illustrated in FIG. 1B, the complex amplitude and phase of the sample speckle field will fluctuate as a function of time. The effect of this fluctuation will be to create a new sample speckle pattern measurement that will have a lower average magnitude than the static case, since the integrated sample electric field will effectively result in the summation of a random walk in the complex plane at each speckle grain where the amplitude and phase of the phasor is drawn from the corresponding statistical distributions known for speckle (e.g., Rayleigh distributed amplitude and uniformly distributed phase).

Defining the heterodyne signal as:

$$S(r) = \frac{1}{T}\int_0^T 2E_0(r)E_s(r, t)\cos(k \cdot r - \phi_s(r, t))dt \quad \text{(Eqn. 3)}$$

The second moment of $S(r)$ contains the field decorrelation function $g_1(t)$:

$$\langle S(r)^2 \rangle = \frac{4E_0^2}{T^2}\Big\{\int_0^T\int_0^T E_s(r, t_1)\cos(k \cdot r - \phi_s(r, t_1))E_s(r, t_1)\cos(k \cdot r - \phi_s(r, t_1))dt_1 dt_1\Big\} \quad \text{(Eqn. 4)}$$

$$= \frac{4E_0^2 \overline{E_s^2}}{T}\int_0^T 2\Big(1 - \frac{t}{T}\Big)(g_1(t))^2 dt$$

$$= \frac{4\overline{I_0}\overline{I_s^2}}{T}\int_0^T 2\Big(1 - \frac{t}{T}\Big)(g_1(t))^2 dt$$

As shown in Eqn. 4, the second moment of $S(r)$ is a function of the integrated value of $g_1(t)$ over the exposure time, weighted by a factor inversely proportional to the exposure time T. In the case where our sample field is a speckle pattern, the second moment is a measure of the blurring of the speckle pattern. If the sample is slowly decorrelating over the exposure time (i.e., $g_1(t) \approx 1$ for $0 < t < T$), then the result of the integral is:

$$\langle S(r)^2 \rangle = \frac{4I_0 \overline{I_s}}{T}\int_0^T 2\Big(1 - \frac{t}{T}\Big)(g_1(t))^2 dt \quad \text{(Eqn. 5)}$$

$$= \frac{4I_0 \overline{I_s}}{T} \cdot T$$

$$= 4I_0 \overline{I_s}$$

As the decorrelation time increases and the value of $g_1(t)$ begins to significantly decay from 1 during the exposure time T, the value of $\langle S(r)^2 \rangle$ will decrease. In the limit where the value of $g_1(t)$ decays quickly to 0 relative to the exposure time, the value of $\langle S(r)^2 \rangle$ decays to zero. Therefore, by measuring the second moment of the sample speckle field, the decorrelation time can be inferred.

Another Example

Another way to express the total instantaneous interference pattern $I_t(r)$ at the position $r = (x, y)$ in the observation plane is:

$$I_t(r) = |E_r|^2 + |E_s(r)|^2 + 2|E_r||E_s(r)|\cos(k_0 \times \sin\theta\, x + \phi_s(r)) \quad \text{(Eqn. 6)}$$

$$= I_R + I_S(r) + 2\sqrt{I_R I_S(r)}\,\cos(k_0 \times \sin\theta + \phi_s(r))$$

where $E_R$ is the complex light field of the plane wave reference beam, $E_S(r)$ is the complex light field of the sample beam, $\phi_s(r)$ is the phase difference between the reference beam and the sample beam, $k_0$ is the wave vector corresponding to the tilted plane wave reference beam, and $\theta$ is the oblique tilt angle of the reference beam.

The interference pattern recorded by the camera is:

$$I(r) = \int_0^T (|E_r|^2 + |E_s(r;t)|^2 + 2|E_r||E_s(r;t)|\cos(k_0 \times \sin\theta x + \phi_s(r, t)))dt \quad \text{(Eqn. 7)}$$

The interference signal $H(r)$ is defined as:

$$H(r) = \frac{1}{T}\int_0^T (2|E_r||E_s(r, t)|\cos\phi_s(r, t))dt \quad \text{(Eqn. 8)}$$

$$= \frac{1}{T}\int_0^T (|E_r||E_s(r, t)|\exp(i\phi_s(r, t))dt +$$

$$\frac{1}{T}\int_0^T (|E_r||E_s(r, t)|\exp(-i\phi_s(r, t))dt$$

By selecting the first conjugate pair, the iSVS signal $S(r)$ can be defined as:

$$S(r) = \frac{1}{T}\int_0^T (|E_r||E_s(r, t)|\exp(i\phi_s(r, t))dt \quad \text{(Eqn. 9)}$$

In one example, the field decorrelation can be defined as:

$$g_1(t) = \frac{\langle E_s(r, t_0)E_s^*(r, t_0 + t)\rangle}{\langle |E_s(r, t_0)|^2\rangle_{t_0}} \quad \text{(Eqn. 10)}$$

The second moment of the iSVS signal $S(r)$ contains the field decorrelation as:

$$\langle S(r)^2 \rangle = \frac{I_R}{T^2}\Big\{\int_0^T\int_0^T dt_1 dt_2\, |E_s(r, t_1)|\exp(i\phi_s(r, t_1)) E_s(r, t_2)\exp(-i\phi_s(r, t_2))\Big\} \quad \text{(Eqn. 11)}$$

$$= \frac{I_R \overline{I_s}}{T}\int_0^T 2\Big(1 - \frac{t}{T}\Big)g_1(t)dt$$

where $\langle \cdot \rangle_{t_0}$ denotes the expected value over $t_0$, $\langle \cdot \rangle$ denotes the expected value space, $I_R$ is the intensity of the reference beam, $\overline{I_s}$ is the mean intensity of the signal beam. Both of $I_R$ and $\overline{I_s}$ can be determined from a calibration operation such as the calibration operation discussed in Section III.

An interference fringe visibility factor F is defined as:

$$F = \frac{\langle S(r)^2 \rangle}{I_R \overline{I_s}} = \frac{1}{T}\int_0^T 2\Big(1 - \frac{t}{T}\Big)g_1(t)dt \quad \text{(Eqn. 12)}$$

The interference fringe visibility factor F ranges from 0 (minimum visibility) to 1 (maximum visibility) depending on $g_1(t)$. If the sample is static (i.e., $g_1(t) = 1$ or about 1 for $0 < t < T$), the interference fringe visibility factor $F = 1$ or about 1 respectively. If the complex field of the sample light field is decorrelating, the interference fringe visibility factor F will be less than 1, e.g., in a range from about zero to about 1.0. If the complex field of the sample light field is decorrelating quickly as compared to the exposure time T, for example, where $g_1(t) = 1$ or nearly 1 for $0 < t < \tau$ and $g_1(t) = 0$ or nearly 0 for $\tau < t < T$ where $\tau \ll T$), then the visibility factor can be expressed as $$F = \frac{2\tau}{T}.$$

In this case, multiple decorrelation events within a single camera exposure time may blur the inference fringes, yielding low fringe visibility.

Example Applications of iSVS Systems and/or Methods

1) Blood Flow Example

Scattered light can be directly analyzed to yield functional information about activity within tissue. For example, the measured dynamics of cerebral blood flow (CBF) within brain tissue can be used as an indication of neuronal activity, providing non-invasive functional information.

According to one aspect, interferometric speckle visibility spectroscopy (iSVS) methods and/or systems can perform interferometric measurements that enable sensitive, high-speed monitoring of blood flow dynamics. The dynamics of blood flow within tissue are a key indicator of metabolic function, providing functional information about physiological activity. In certain implementations, iSVS methods and/or systems can be used to measure blood flow dynamics non-invasively using the dynamic properties of a captured optical field that has interacted with blood in a volume of interest. Certain embodiments of iSVS systems and methods described herein implement a large-pixel-count camera and/or implement a reference beam to interfere with scattered light from the sample to enable high-sensitivity measurement of the decorrelation inside the sample such as tissue, even at low light intensities.

2) Atmospheric Measurements Example

According to another aspect, interferometric speckle visibility spectroscopy (iSVS) methods and systems can perform interferometric measurements that enable high-sensitivity measurement of the decorrelation for evaluation of atmospheric dynamics. An example of a technique that can be implemented to determine the atmospheric dynamics from the correlation determined by an iSVS system and/or method can be found in Ancellet, Gerard M. and Menzies, Robert T., "Atmospheric correlation-time measurements and effects on coherent Doppler lidar," J. Opt. Soc. Am. A 4, 367-373 (1987), which is hereby incorporated by reference in its entirety.

III. Interferometric Speckle Visibility Spectroscopy (iSVS) Methods

Certain aspects pertain to iSVS methods that include operations for determining sample dynamics from one or more off-axis interferograms. According to one aspect, an iSVS method includes (i) recovering sample speckle field data from an off-axis interferogram recorded over a single exposure time, and (ii) determining sample dynamics from speckle statistics of the sample speckle field data. The off-axis interferogram captured by the camera includes both sample speckle field data and reference beam data. The iSVS method performs Fourier transform on the off-axis interferogram to reveal off-axis lobes that contain sample speckle field data and a third central lobe with reference beam data. The iSVS method may then extract the sample speckle field data from at least one of the off-axis lobes and determine sample dynamic from statistics calculated from the sample speckle field data.

Although the iSVS methods in some of the examples of this Section are described as determining sample dynamics from a single off-axis interferogram, it would be understood that the disclosure is not so limiting. In other implementations, the iSVS methods can determine sample dynamics for each off-axis interferogram of a plurality of off-axis interferograms captured at different exposure times or captured during a single exposure time. In one such implementation, an iSVS method may further include determining a change in sample dynamics. For example, an iSVS method may calculate the movement speed of an object in the sample during different exposure times to determine the change of movement speed over time, e.g., to take a measurement of pressure or to measure the solidification or changes in a substance such as a gel due to temperature.

Figure 2:
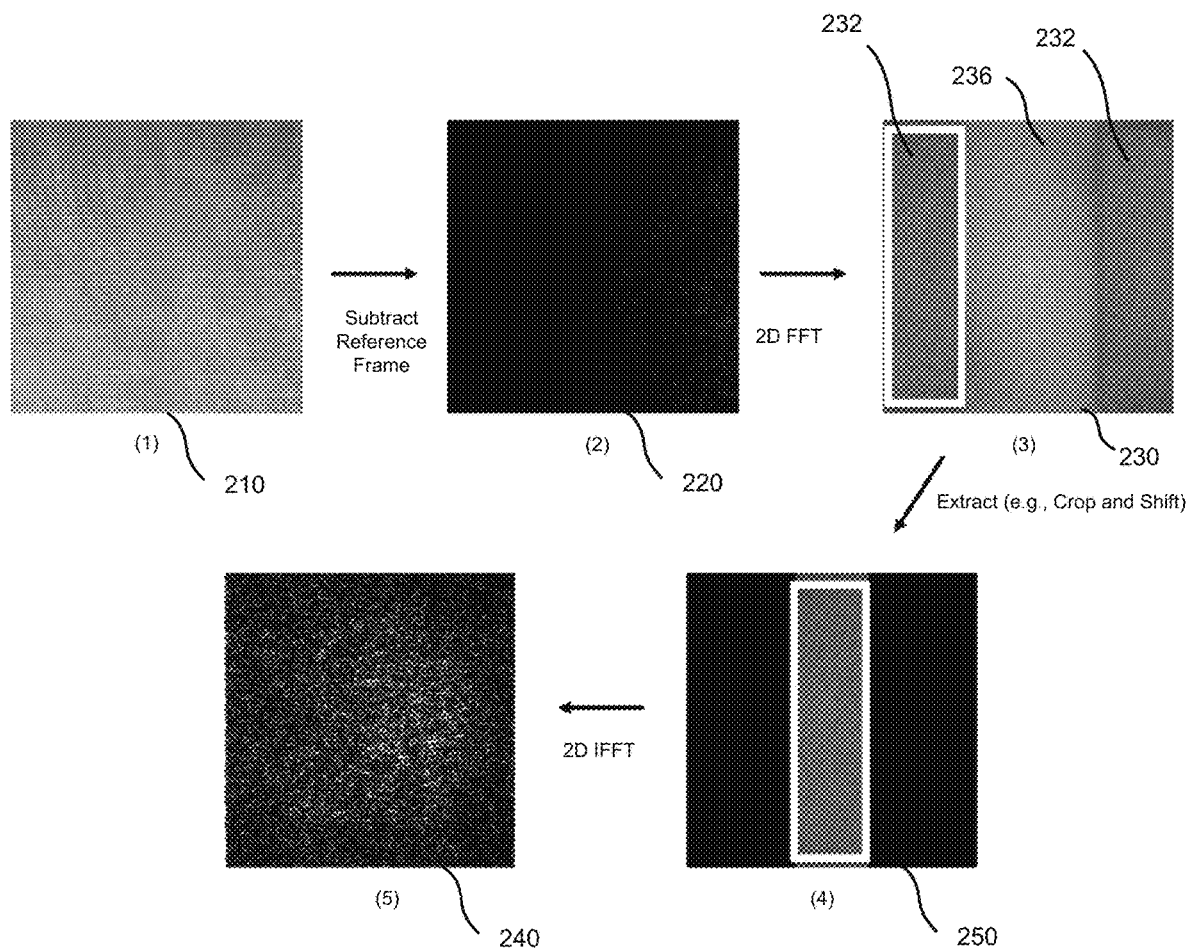
FIG. 2 is a schematic diagram illustrating an example of a sequence of operations of an iSVS method for recovering a sample speckle field pattern from an off-axis interferogram recorded during a single exposure time, according to one embodiment.

FIG. 2 illustrates an example of a sequence of operations of an iSVS method used to recover a sample speckle field pattern from an off-axis interferogram recorded during a single exposure time, according to one embodiment. In FIG. 2, the sequence of the operations is denoted by directional arrows through depicted images 210, 210, 230, 240, and 250. In this illustrated example, the sequence of operations includes a first operation of subtracting a reference frame from the off-axis interferogram, depicted as image 210, to generate a reference-subtracted image, depicted as image 210. The reference frame may be, for example, a 2D image having a uniform intensity that is equal to the reference beam intensity. This operation can suppress noise from non-uniformities in the reference beam which may additionally avoid noise within the range of spatial frequencies that contain the sample signal. In another embodiment, this first operation is omitted, for example, in implementations where there is little to no noise.

The sequence of operations illustrated in FIG. 2 also includes Fourier transforming (e.g., using 3D fast Fourier transform) the reference-subtracted image, depicted as image 220, to generate a Fourier-transformed reference-subtracted image, depicted as image 230. The Fourier-transformed data, depicted as image 230, includes a first off-axis lobe 232 and a second off-axis lobe 234, and a third lobe 236. The three lobes 232, 234, 236 include data of the reference beam and the sample beam. The first off-axis lobe 232 and the second off-axis lobe 234 contain the sample field data. The third lobe 236 contains the reference beam data. The illustrated sequence of operations also includes extracting the sample field data from one of the off-axis lobes 232, 234 and dividing by the amplitude of the reference beam to yield sample amplitude only. In one case, the sample field data from one of the off-axis lobes 232, 234 is spatially cropped, shifted to the center of the spatial frequency space to remove the phase ramp of the reference beam in the spatial domain, and divided by the amplitude of the reference beam.

In certain implementations, the iSVS method includes a cropping operation to extract a sample field data from at least one of the off-axis lobes in a off-axis interferogram in the frequency domain. The known tilt angle of the reference beam and the size of the rectangular aperture mask are used to determine the correct area of the spatial frequency domain to filter out. A spatial frequency filter based on this determined area of the spatial frequency domain can be used to crop the data.

The sequence of operations illustrated in FIG. 2 also includes inverse Fourier transforming the extracted data back to the spatial domain, yielding an image of the complex amplitude and phase of the sample speckle field. The magnitude of the sample speckle field is directly related to the decorrelation time of the light contributing to it. In one aspect, one or more additional operations may be included to perform analysis of different spatial locations using the data from the complex amplitude and phase of the sample speckle field. The complex amplitude and phase of the sample speckle field includes data at different spatial locations that can represent contributions from different areas and path length distributions and can be used to extract more information from the sample. For example, this can be used to map the blood flow at different locations in the brain, indicating the activity of different parts of the brain.

According to one aspect, an iSVS method determines a decorrelation time from the sample speckle field data in the spatial frequency domain and/or from the image of the sample speckle field pattern in the space domain. The magnitude of the sample speckle field pattern is directly related to the decorrelation time of the light contributing to it. In one implementation, the iSVS method determined the decorrelation time of a given area of the sample speckle field pattern by calculating the average of the sample electric field magnitude within that area and determining the decorrelation time from the calculated sample electric field magnitude within that area using e.g., a mapping of different values of sample electric field magnitude corresponding to different decorrelation times. For example, the iSVS method may use a lookup table with mappings of different visibility factors F to different decorrelation times to determine the decorrelation time corresponding to the calculated average magnitude in that area. These mappings can be inferred from Eqn. 12 where decorrelation time $\tau$ is linked to fringe visibility. In one aspect, an iSVS method may calculate a decorrelation time for each of multiple areas and/or calculate multiple decorrelation times during each exposure time for each of one or more areas.

Figure 3:
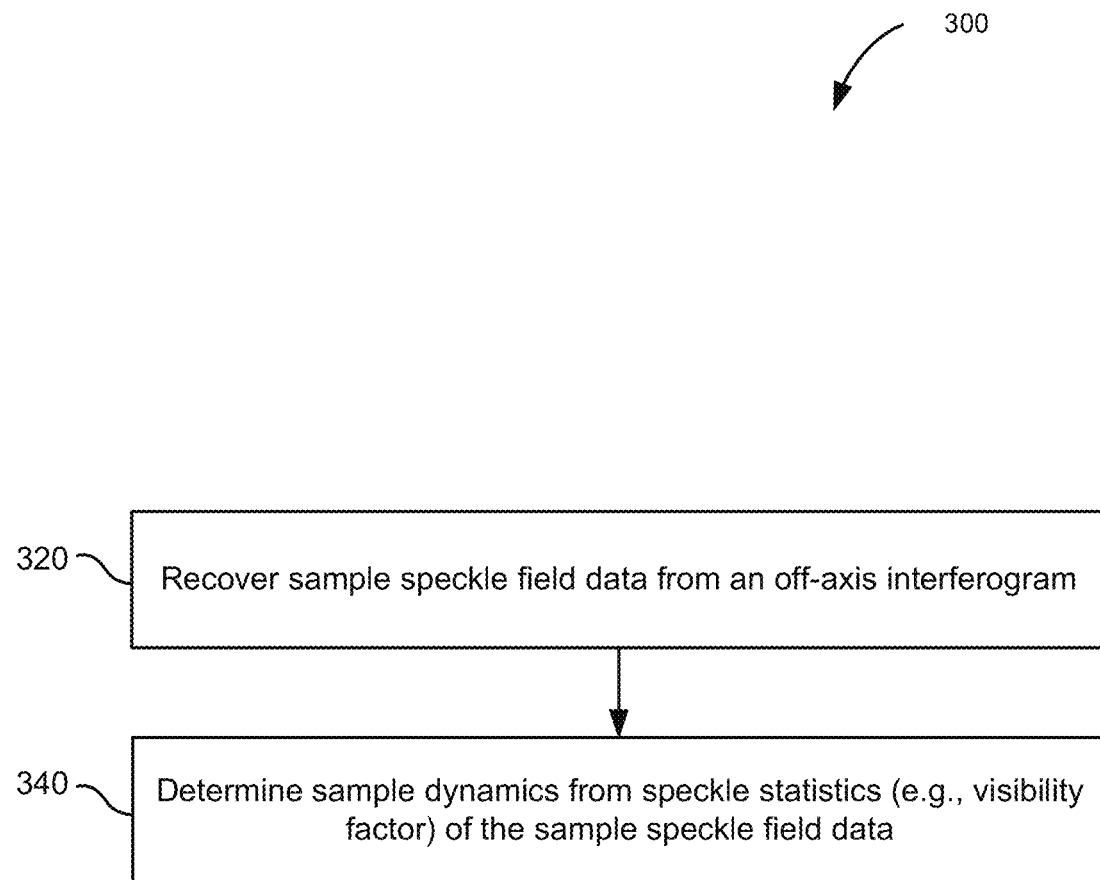
FIG. 3 is a flowchart depicting operations of an iSVS method, according to implementations.

FIG. 3 is a flowchart depicting operations of an iSVS method implemented by an iSVS system, according to certain implementations. One or more processors of the iSVS system may execute instructions that cause the one or more processors to perform the operations of the iSVS method. Although the iSVS method is described with reference to recovering sample speckle field data from one off-axis interferogram and determining sample dynamics from statistics of taken from the sample speckle field data, it would be understood that the disclosure is not so limiting. In another aspect, the iSVS method may recover sample speckle field data from a plurality of off-axis interferograms respectively and determine sample dynamics from the sample field data determined from each off-axis interferogram by applying the same operations as described with respect to FIG. 3. The iSVS method may also include receiving the off-axis interferogram from the camera or receiving or retrieving the off-axis interferogram from memory, according to one implementation. In certain implementations, the off-axis interferogram is a two-dimensional image captured by, e.g., a two-dimensional light detector array of a camera of an iSVS system. An example of a suitable two-dimensional light detector array is a CCD array. The iSVS method may also include sending control signals to the camera to activate recording of one or more off-axis interferograms.

At operation 320, sample speckle field data is recovered from an off-axis interferogram recorded during a single exposure time. For example, the iSVS method may recover the sample speckle field data by Fourier transforming the off-axis interferogram to generate data with off-axis lobes containing the sample speckle field data and extracting at least one of the off-axis lobes from the spatial frequency space. Optionally, the sample speckle field pattern may be reconstructed by inverse Fourier transforming the extracted sample speckle field data.

At operation 340, sample dynamics are determined from speckles statistics calculated from the sample speckle field data or from the sample speckle pattern recovered. An example of a speckle statistics includes an average or mean magnitude within a given area of the sample speckle pattern. The area may be a portion of the sample speckle pattern according to one aspect, or may be the entire sample speckle pattern according to another aspect. Other examples of speckle statistics include the standard deviation or additional moments of the distribution. An example of sample dynamics is a decorrelation time of the sample speckle pattern or one or more areas of the sample speckle pattern. Another example of sample dynamics is movement speed of one or more objects in the sample. In one aspect, movement speed may be calculated from the calculated decorrelation time. In one aspect, the sample dynamics determined at operation 340 include one or more of a decorrelation time, a movement of one or more object in a sample, the changes in the sample due to temperature, or the changes in a sample due to solidification or phase change.

In one aspect, operation 340 includes calculating speckle statistics from the sample speckle field data or the sample speckle pattern and determining the sample dynamics using the speckle statistics and/or other data. For example, operation 340 may calculate the average or mean magnitude of a given area of the sample speckle pattern reconstructed and determine a correlation speed from the average or mean magnitude of the values of the sample speckle pattern in the given area. In one case, operation 340 may also calculate the movement of one or more objects in the sample based on the correlation speed determined. According to one aspect, the iSVS method uses a calibrated mapping between the sample dynamics and the speckle statistics and/or other data to determine the sample dynamics.

Figure 4:
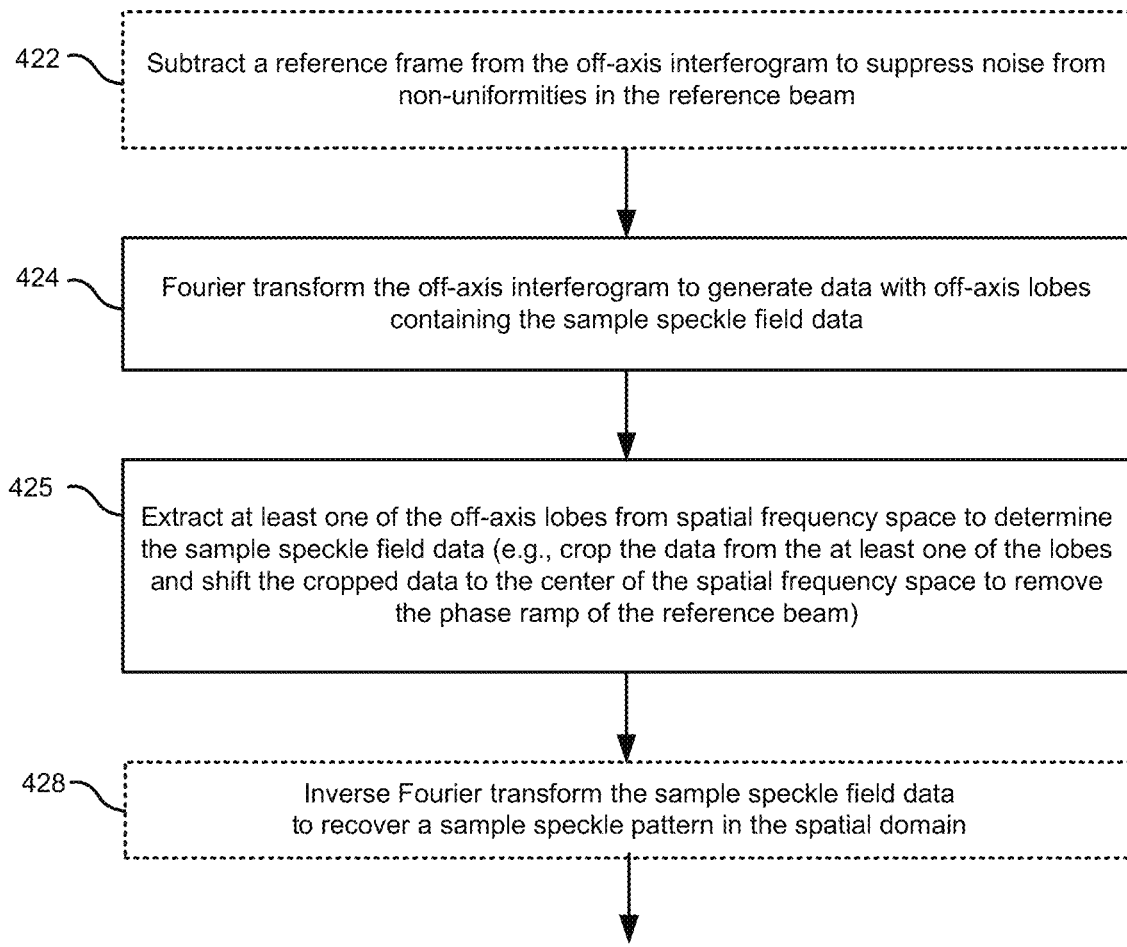
FIG. 4 is a flowchart depicting sub-operations of an operation of an iSVS method, according to an implementation.

FIG. 4 is a flowchart depicting an example of sub-operations that may be included in operation 320 of FIG. 3, according to certain aspects. Sub-operations depicted by dotted line boxes are optional.

At optional (denoted by the dotted line) sub-operation 422, the iSVS method subtracts a reference frame from the off-axis interferogram. Subtracting the reference frame from the off-axis interferogram may suppress noise from non-uniformities in the reference beam. The reference frame is an interferogram where the sample beam has been blocked. Therefore, only the reference beam is illuminating the sensor and any non-uniformities can be captured.

At sub-operation 424, the iSVS method performs Fourier transformation (e.g. using fast Fourier transform) on the off-axis interferogram to generate data in the spatial frequency domain with off-axis lobes containing sample speckle field data. The iSVS system includes a vertical slit at the Fourier plane that sets the shape of the sample spectrum (e.g., a rectangular vertical slit sets a rectangular shape of the sample spectrum and a circular vertical slit sets a circular shape of the sample spectrum). The raw off-axis interferogram captured by the camera of the iSVS system includes both sample speckle field and reference beam data. The tilt angle of the reference beam can be designed, according to one aspect, to position the off-axis lobes containing sample speckle field data to the sides of the spatial frequency spectrum without overlapping with other terms.

At sub-operation 425, the iSVS method extracts sample speckle field data from the at least one of the off-axis lobes in the spatial frequency domain. In one implementation, the iSVS method extracts the sample speckle field data by spatially cropping one of the off-axis lobes from the image, shifting the cropped data to the center of the spatial frequency space, which can remove the phase ramp of the reference beam in the spatial domain, and then divide the data by the amplitude of the reference beam. In addition or alternatively, the iSVS method may select one of the off-axis lobes. In other implementations, the data from the off-axis lobe may be extracted by YoonSeok Baek, KyeoReh Lee, Seungwoo Shin, and YongKeun Park, "Kramers-Kronig holographic imaging for high-space-bandwidth product," Optica 6, 45-51 (2019), which is hereby incorporated by reference in its entirety.

At sub-operation (denoted by dotted line) operation 426, the iSVS method inverse Fourier transforms (e.g. using fast Fourier transform) the data to recover an image of complex amplitude and phase of the sample speckle field. The magnitude of the sample speckle field is directly related to the decorrelation of the light contributed to it. With the image of the complex amplitude and phase of the sample speckle field, evaluation of speckle statistics and sample dynamics at different spatial locations of the sample can be performed. For example, in some implementations, the iSVS method may determine the decorrelation time for one or more areas of the sample and then determine the movement speed of an object or objects in the one or more areas from the decorrelation times.

Figure 5:
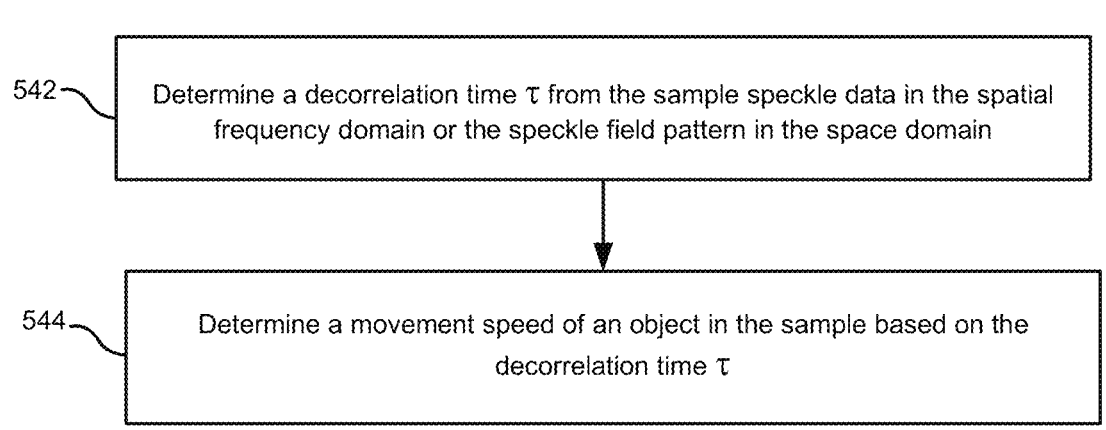
FIG. 5 is a flowchart depicting sub-operations of an operation of an iSVS method, according to an implementation.

FIG. 5 is a flowchart depicting an example of sub-operations that may be included in operation 340 of FIG. 3, according to certain aspects. At sub-operation 542, the decorrelation time $\tau$ is determined. The decorrelation time $\tau$ can be determined from the sample speckle field data in the spatial frequency domain or from data taken from the image of the complex amplitude and phase of the sample speckle field in the space domain. In one implementation, the iSVS method determines the decorrelation time $\tau$ for one or more spatial coordinates or areas of the sample using the image of the sample speckle field reconstructed, e.g., from sub-operation 426. In this case, the iSVS method calculates the average of the sample electric field magnitude within each of the one or more areas and then determines the decorrelation time from the calculated sample electric field magnitude within those one or more areas using e.g., a mapping of different values of sample electric field magnitude corresponding to different decorrelation times. This mapping is described in Eqn. 12 by the relationship between the sample decorrelation function $g_1(t)$ and the fringe visibility. The magnitude maps to the decorrelation time with smaller and larger field amplitudes signifying shorter and longer decorrelation times respectively.

At sub-operation 544, the iSVS method calculates a movement speed of an object or objects in the sample based on the decorrelation time $\tau$ determined from the sample speckle pattern. For example, the cerebral blood flow can be calculated using the decorrelation time $\tau$. A method of calculating cerebral blood flow from decorrelation time $\tau$ can be found in Selb, J., Boas, D. A., Chan, S.-T., Evans, K. C. Buckley, E. M., Carp, S. A., "Sensitivity of near-infrared spectroscopy and diffuse correlation spectroscopy to brain hemodynamics: simulations and experimental findings during hypercapnia," *Neurophotonics*. 1, 15005 (2014), which is hereby incorporated by reference in its entirety.

Calibration Method

Figure 6:
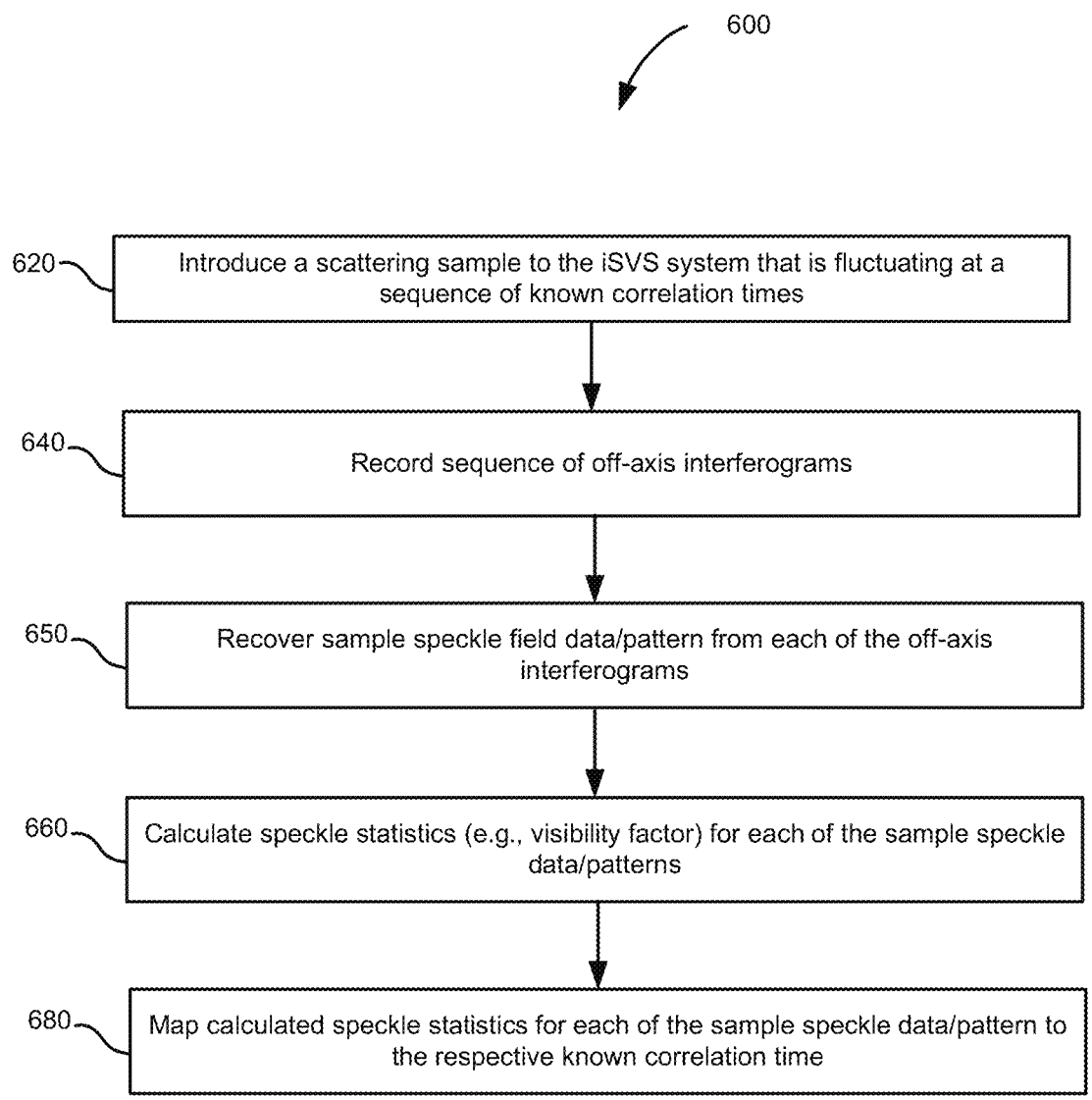
FIG. 6 is a flowchart depicting operations of an iSVS method for calibrating an iSVS system, according to an implementation.

Certain aspects pertain to methods for calibrating an iSVS system to compare or map results (e.g., speckle statistics) from operating the iSVS system and/or performing an iSVS method to different values of sample dynamics such as decorrelation times). FIG. 6 is a flowchart depicting operations of an iSVS method for calibrating an iSVS system to map effective visibility factors to different decorrelation times, according to an implementation.

At operation 620, a scattering sample (or samples) that is fluctuating at a sequence of known decorrelation times or a calibration subsystem simulating such as sample is introduced into an iSVS system. In one example, different driving voltages are applied sequentially to a motor driving a rotating diffuser to produce sample fluctuations at a sequence of different correlation times where each driving voltage causes a different correlation time. The decorrelation times of the sample can be measured by another system such as a DCS system that measures the time trace of the fluctuations using a single photon counting module.

Figure 10A:
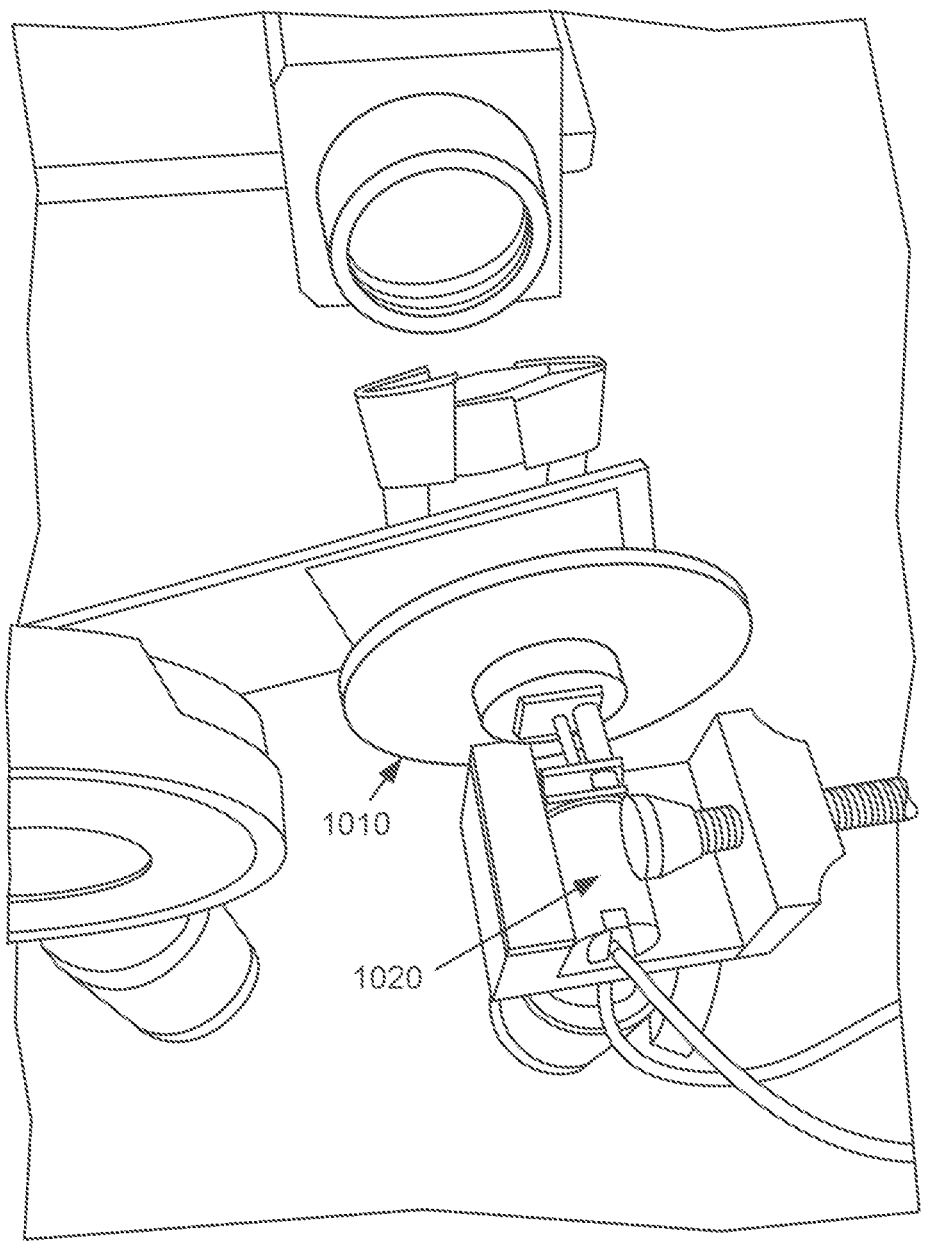
FIG. 10A is a photograph of an examples of components of a calibration subsystem of an iSVS system including a rotating diffuser and a motor and gearbox, according to one aspect.

FIG. 10A is a photograph of an example of components of a calibration subsystem of an iSVS system including a rotating diffuser 1010 and a motor and gearbox 1020, according to one aspect. The motor and gearbox 1020 are in in electrical communication with the rotating diffuser 1010 to apply one or more driving voltages. In response, the rotating diffuser 1010 rotates at a sequence of different speeds, which simulates sample fluctuations corresponding to a sequence of correlation times.

Figure 10B:
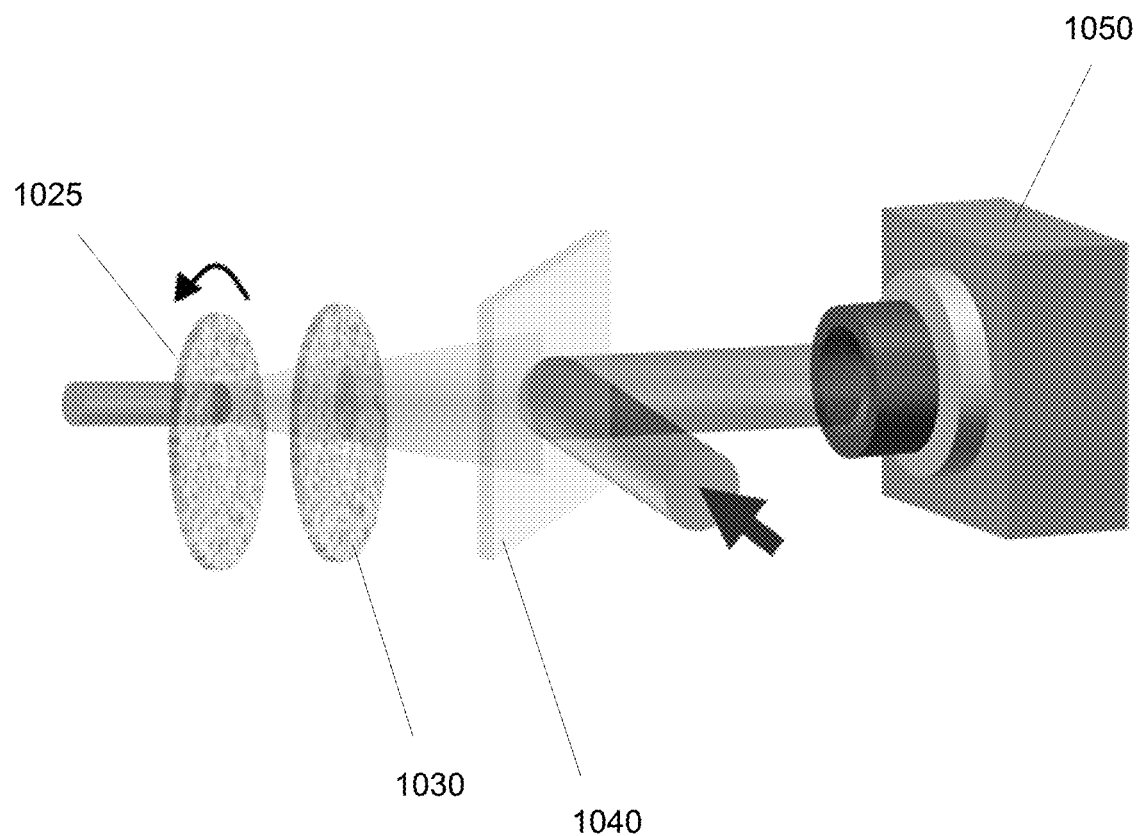
FIG. 10B is a schematic diagram of an example of components of a calibration subsystem of an iSVS system, according to one aspect.

FIG. 10B is a schematic diagram of an example of components of a calibration subsystem of an iSVS system, according to one aspect. In this example, the calibration subsystem includes a first rotating diffuser 1025, a second static diffusor 1030, a beam splitter 1040, and a camera 1050. An example of diffusers that can be used are glass diffusers such as the DG20 Series ground glass diffusers made by Thorlabs. The first rotating diffuser 1025 has controlled rotating speeds and the second static diffusor 1030 is static. During calibration, a laser beam illuminated the first rotating diffuser 1025 and a range of rotation speeds was applied. The scattered light from the first rotating diffuser 1025 illuminated the second static diffuser 1030 and was collected by an optical system. The second static diffuser 1030 is used to eliminate the speckle pattern "smearing" effect that is present when using a single rotating diffuser. The decorrelation times were computed by measuring the time traces of the intensity fluctuations using a single photon counting module (SPCM) in the optical setup. An example of a commercially-available SPCM is the SPCM-AQRH-14 sold by PerkinElmer. By mapping rotation speed to the measured decorrelation time, a dynamic sample can be simulated with known decorrelation times.

Figure 11:
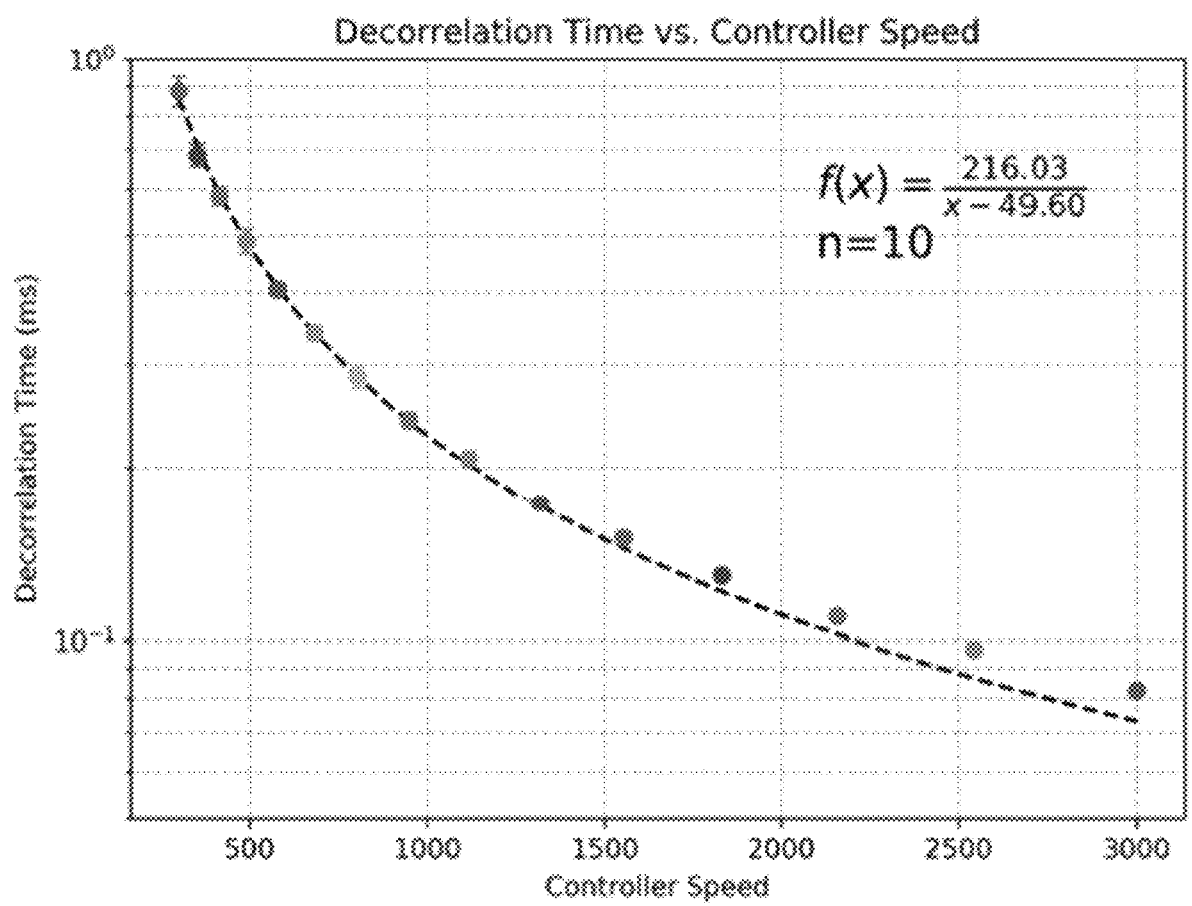
FIG. 11 is a graph with a plot of decorrelation times measured by a calibration subsystem for different motor speeds controlled by control signals from a motor controller in communication with the motor, according to one aspect.

FIG. 11 is a graph with a plot of decorrelation times measured for different motor speeds controlled by control signals from a motor controller in communication with the motor, according to an implementation. The graph includes mean and standard deviations for each motor speed.

Returning to FIG. 6, at operation 640, a sequence of off-axis interferograms are recorded by the iSVS system while the sample is fluctuating at the sequence of known decorrelation times respectively. Each of the off-axis interferograms in the sequence is recorded while the sample is fluctuating at one of the known decorrelation times. At operation 650, a sample speckle pattern is recovered from each off-axis interferogram of the sequence of off-axis interferograms. Each sample speckle pattern corresponds to a known decorrelation time. At operation 660, speckle statistics are determined (e.g., visibility factor calculated using Eqn. 12) of each sample speckle pattern. At operation 680, a mapping of the speckle statistics (e.g., visibility factor) for each of the known decorrelation times for the iSVS system is determined.

Figure 12A:
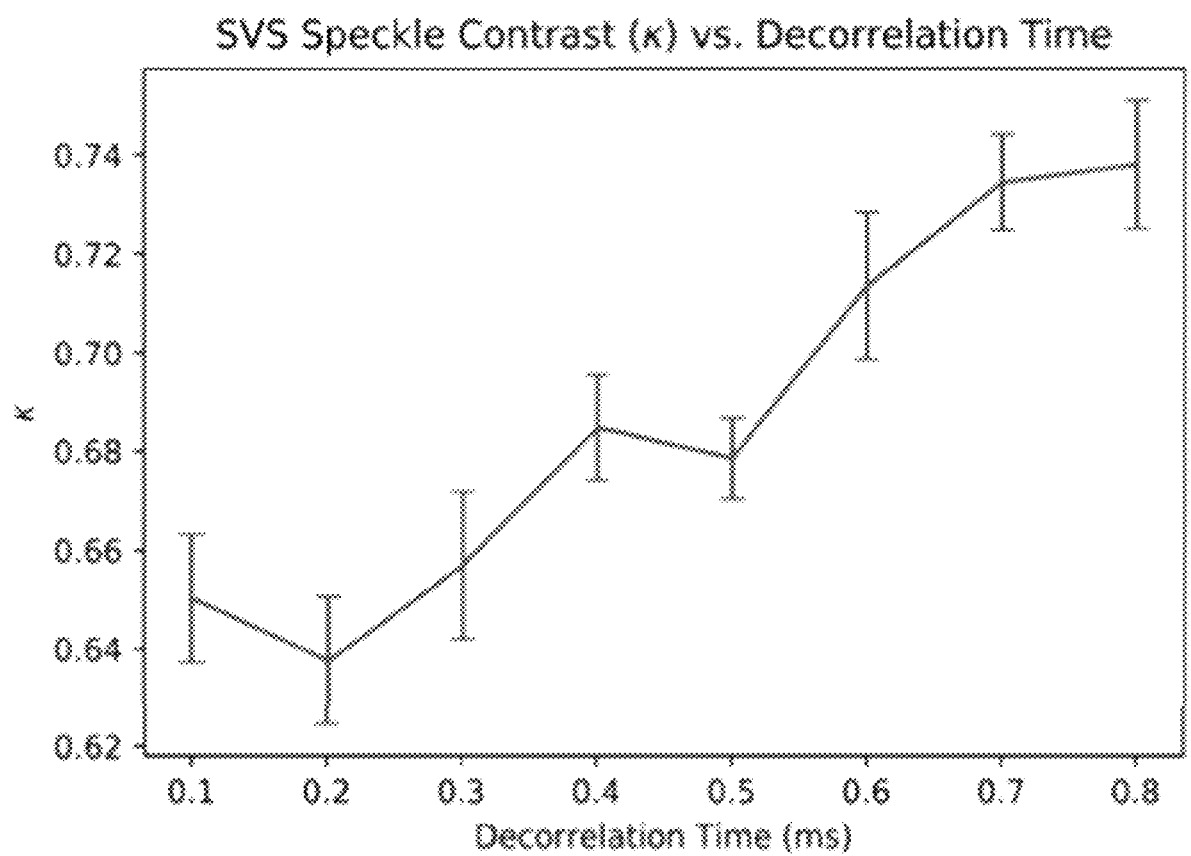
FIG. 12A is a graph of a plot of speckle contrast determined by an SVS system vs. decorrelation time, according an aspect.
Figure 12B:
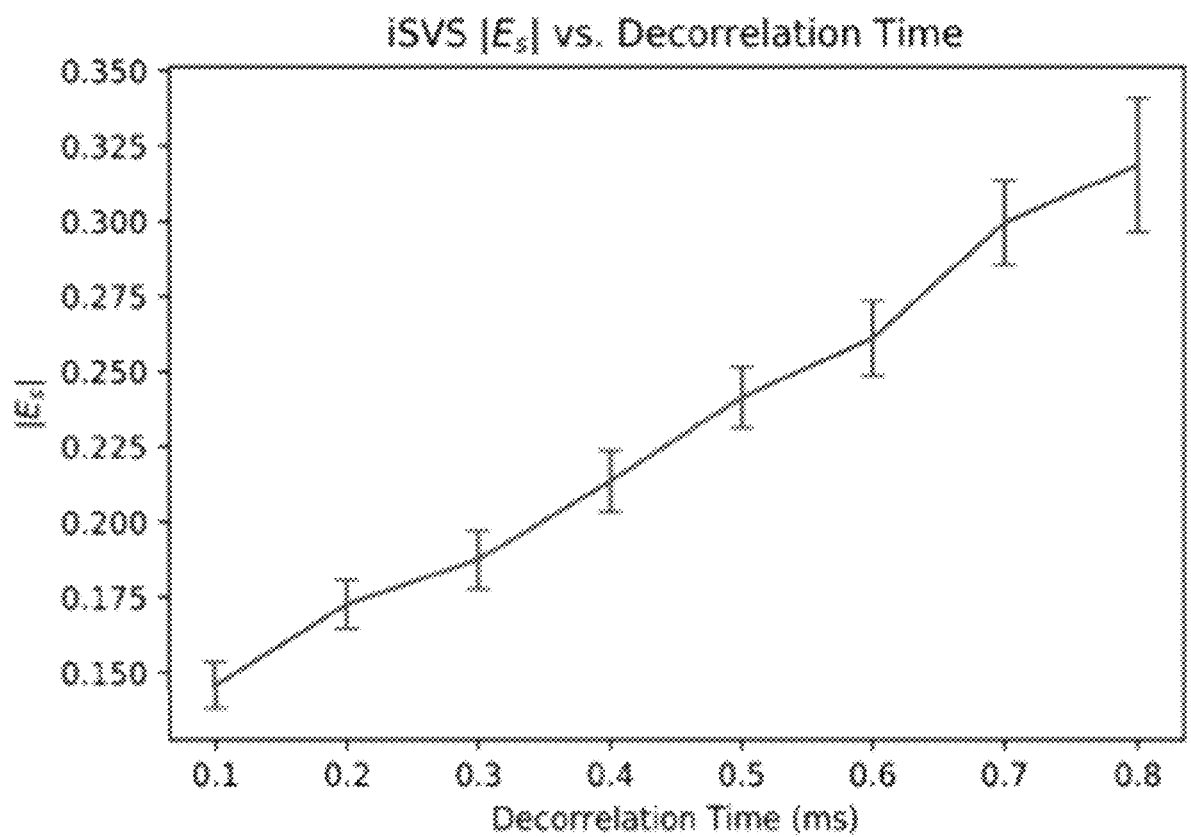
FIG. 12B is a graph with a plot of effective visibility factor determined by an iSVS system vs. decorrelation time as measured by a calibration subsystem, according an aspect.
Figure 13A:
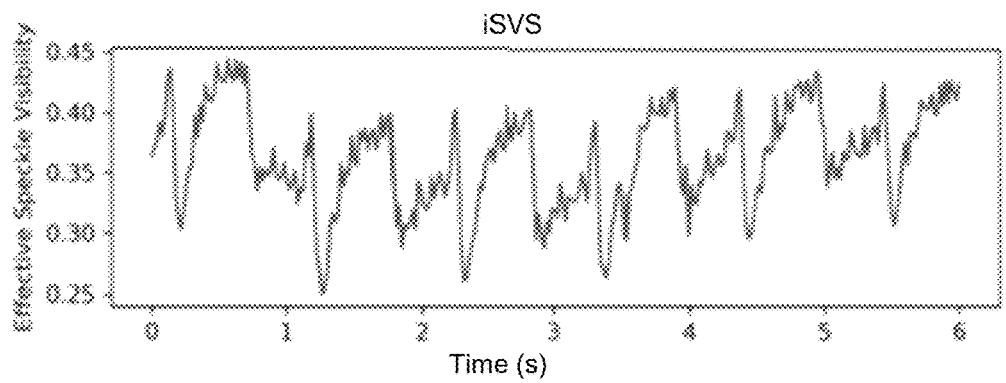
FIGS. 13A, 14A, 15A, 16A, 17A, and 18A are graphs with plots of effective speckle visibility over time (seconds) for the dorsal skin flap as measured by the iSVS system in transmission mode (e.g., iSVS system 900 shown in FIG. 8B) where the laser powers were 1 mW, 0.5 mW, 0.26 mW, 0.13 mW, 0.06 mW, and 0.03 mW respectively, according to implementations.
Figure 13B:
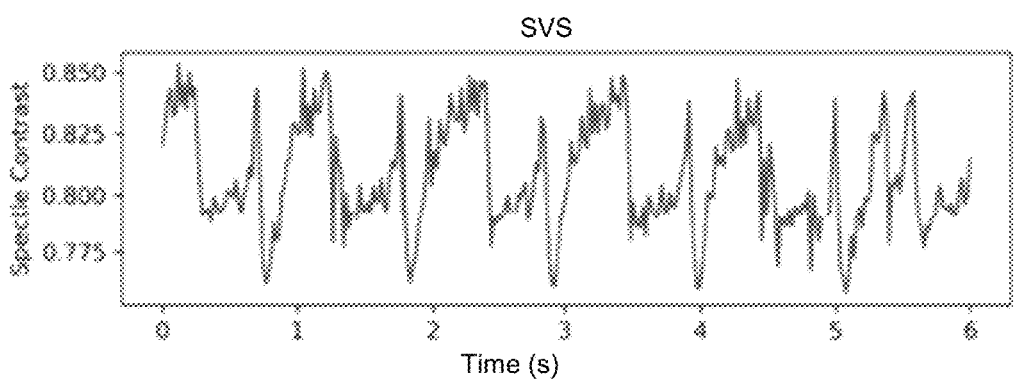
FIG. 13B is a graph with a plot of effective speckle visibility over time (seconds) for a dorsal skin flap as measured by an SVS system in transmission mode where the laser power was 1 mW, according to one example.
Figure 14A:
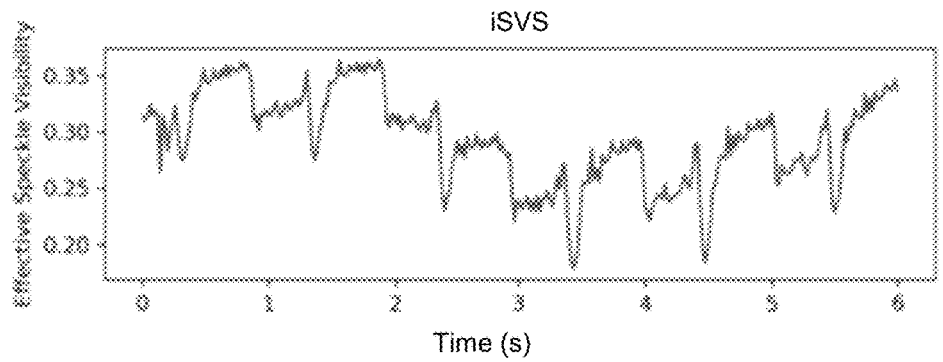
Figure 14B:
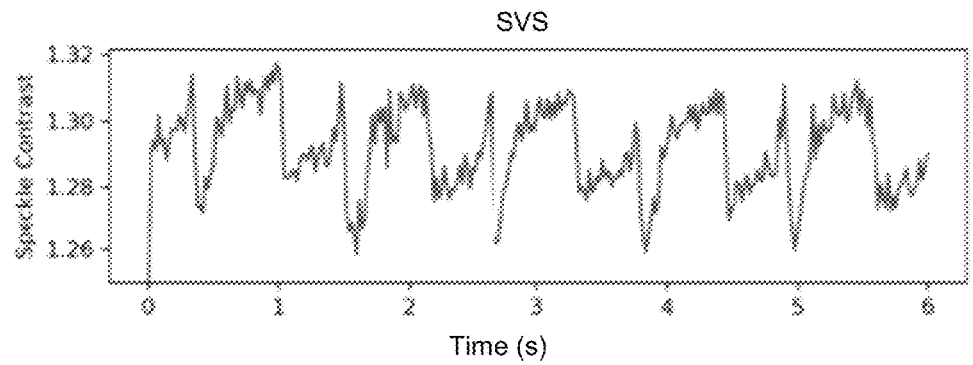
FIG. 14B is a graph with a plot of effective speckle visibility over time (seconds) for a dorsal skin flap as measured by an SVS system in transmission mode where the laser power was 0.5 mW, according to one example.
Figure 15A:
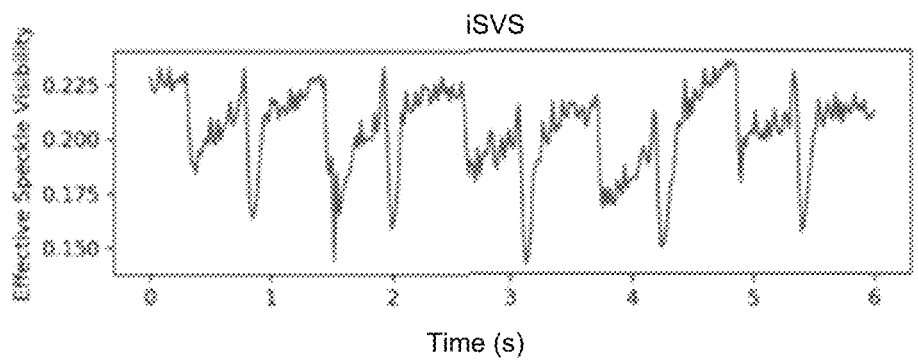
Figure 15B:
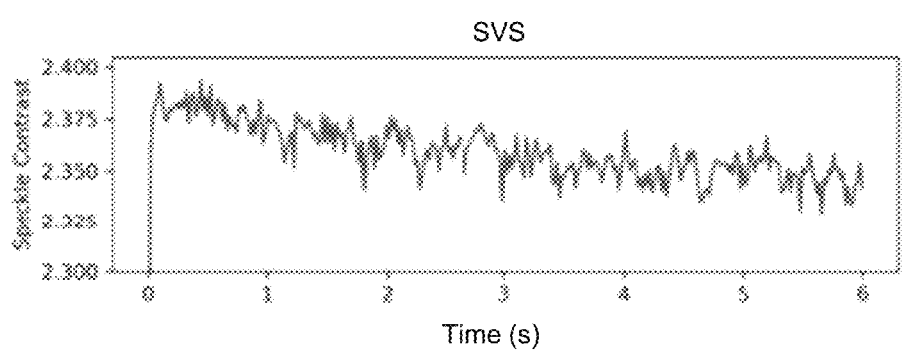
FIG. 15B is a graph with a plot of effective speckle visibility over time (seconds) for a dorsal skin flap as measured by an SVS system in transmission mode where the laser power was 0.26 mW, according to one example.
Figure 16A:
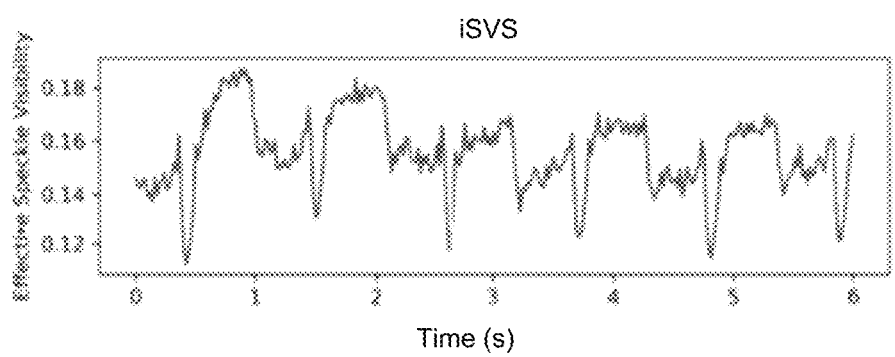
Figure 16B:
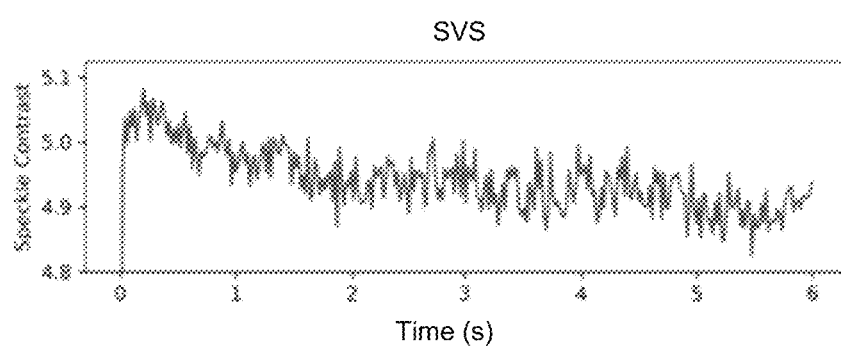
FIG. 16B is a graph with a plot of effective speckle visibility over time (seconds) for a dorsal skin flap as measured by an SVS system in transmission mode where the laser power was 0.13 mW, according to one example.

FIG. 12A is a graph of a plot of speckle contrast determined by an SVS system vs. decorrelation time. FIG. 12B is a graph of a plot of effective visibility factor determined by an iSVS system vs. decorrelation time. The iSVS system was calibrated using the calibration iSVS method depicted by the flowchart shown in FIG. 6. Comparing the error bars on the iSVS curve in FIG. 12B to the SVS curve in FIG. 12A, the iSVS curve resulting from the iSVS method more accurately measured changes in decorrelation times.

IV. Interferometric Speckle Visibility Spectroscopy (iSVS) Systems

Figure 7:
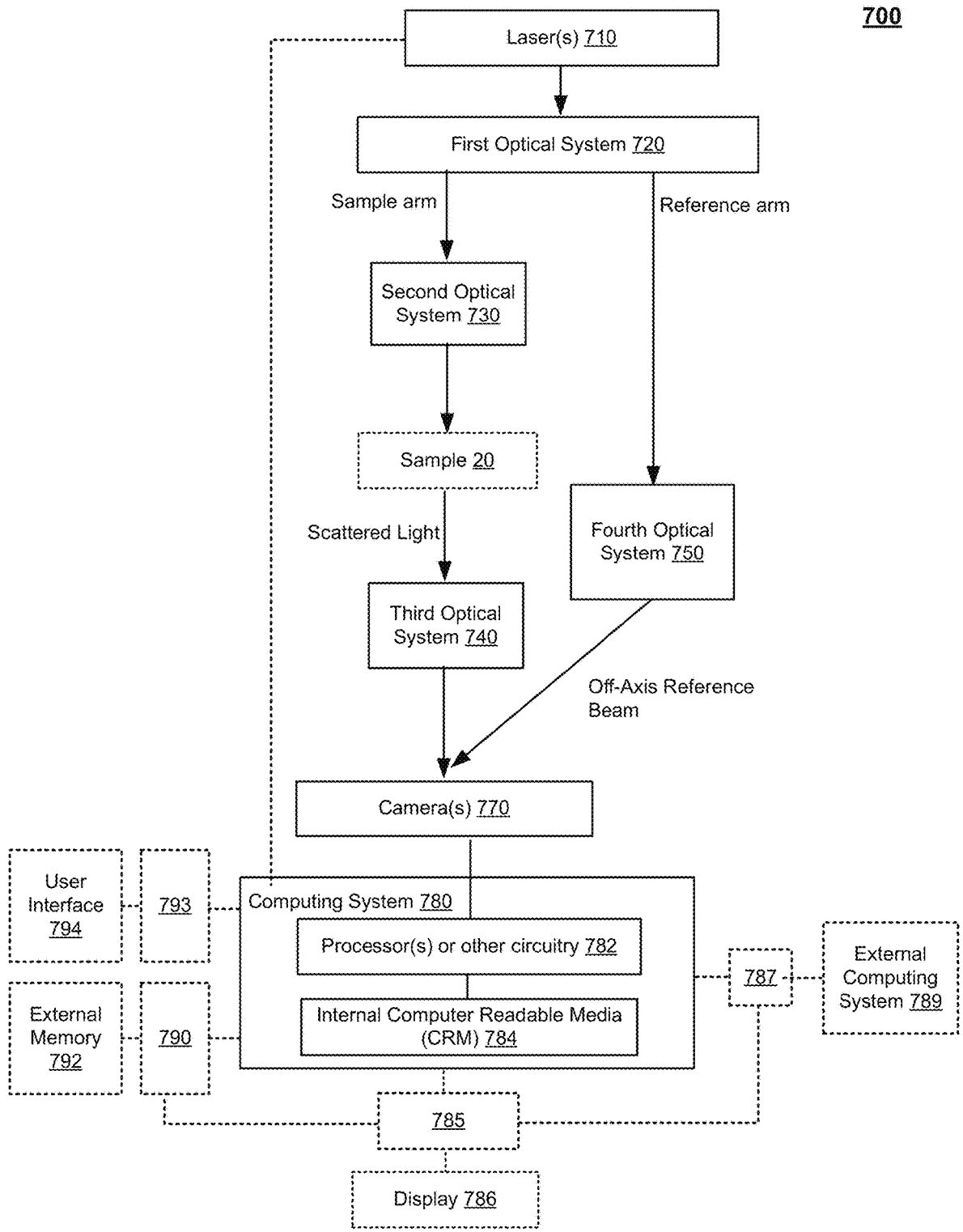
FIG. 7 is a simplified block diagram of components of an iSVS system, according to implementations.

FIG. 7 is a simplified block diagram of components of an iSVS system 700 in an off-axis holographic configuration, according to certain implementations. The iSVS system 700 includes at least one laser 710 for provided a laser beam and a first optical system 720 The first optical system 720 is at least in part configured or configurable to split the laser beam generated by the at least one laser 710 into a sample arm (also referred to herein as a "sample beam") and a reference arm (also referred to herein as a "reference beam"). The first optical system 720 includes one or more optical components (e.g., one or more of a beam splitter, a lens, an optical fiber, mirror, etc.). In one example, the first optical system 720 includes a beam splitter such as, e.g., a polarizing beam splitter that is configured to reflect a first component of the laser beam with a particular polarization direction (e.g. 0 degrees) while transmitting a second component of the laser beam with a perpendicular polarization direction (e.g. 90 degrees). An example of a commercially-available polarizing beam splitter is the polarizing beam splitter PBS251 from Thorlabs.

The iSVS system 700 also includes a second optical system 730 that is at least in part configured or configurable to collect light from the sample beam and relay the light to illuminate the sample 20 being imaged. The second optical system 730 includes one or more optical components (e.g., one or more of a beam splitter, a lens, an optical fiber, mirror, etc.). In one example, the second optical system 730 includes a multimode fiber or a fiber bundle and the sample beam is coupled into the multimode fiber or the fiber bundle and the output beam is collimated and is used to illuminate the sample, e.g., the forehead of a human subject. An example of a suitable multimode fiber is the FB2, M31L02 made by Thorlabs.

During image acquisition, the sample 20 is illuminated by a sample beam. The illustrated example in FIG. 7 is shown at an instant in time during an image acquisition operation of the iSVS system 700. At other times, the sample 20 need not be located at the iSVS system 700 and thus, the sample 20 is depicted as optional by the dotted line. According to one aspect, the sample 20 is illuminated in reflection mode. According to another aspect, the sample 20 is illuminated in transmission mode.

Returning to FIG. 7, the iSVS system 700 also includes a third optical system 740, a fourth optical system 750, one or more cameras 770 having one or more sensors, and a computing system 780. The third optical system 740 is at least in part configured or configurable to collect the sample beam and image the sample beam onto the one or more cameras 770. An example of a commercially-available camera that can be used is the S640 camera made by Phantom. The third optical system 740 includes one or more optical components (e.g., one or more of a beam splitter, a lens, an optical fiber, mirror, etc.). For example, the third optical system 740 may include a multimode optical fiber or a fiber bundle configured to collect the diffused light from the sample. An example of a multimode fiber that can be used is a large core multimode fiber such as M107L02 multimode fiber (e.g., having a core diameter of about 1.5 mm) made by Thorlabs. In this aspect, the multimode fiber is configured to collect light from the sample 20 and relays the light onto the one or more cameras 770. The third optical system 740 may also include, e.g., a 4-f optical subsystem with two or more lenses. In another example, the third optical system 740 may additionally or alternatively include a vertical slit or other aperture located at the Fourier plane of the one or more cameras 770. In this case, the sample beam is imaged onto the camera after being spatially filtered by the aperture in the Fourier plane. The vertical slit or other aperture sets the shape of the sample spectrum in the frequency domain. In this example, the one or more cameras 770 are configured to record one or more interferograms that are low-pass filtered images based on the size and shape of the aperture. The vertical slit can be circular, oval, rectangular, of other geometrical shape. In implementations without a vertical slit or other aperture located at the Fourier plane of the one or more cameras 770, the iSVS system 700 may use a technique such as described in Wenjun Zhou, Oybek Kholiqov, Shau Poh Chong, and Vivek J. Srinivasan, "Highly parallel, interferometric diffusing wave spectroscopy for monitoring cerebral blood flow dynamics," Optica 5, 518-527 (2018), which is hereby incorporated by reference in its entirety. In other words, this experimental setup is also suitable to measure the decorrelation in a standard DCS configuration by measuring the decorrelation time by sampling at high speed in time.

According to certain implementations, the iSVS system includes a laser or lasers. In one aspect, the iSVS system includes a laser that is operable to provide laser light having wavelength between about 650 nm and 950 nm. The 650-950 nm optical window has relatively low optical absorption and therefore enables light to penetrate through the skin, scalp, and skull and interact with the brain. In one example, the laser is a 671-nm laser source that can provide a collimated 56 mW laser beam with a 6-mm spot size that results in a <2 mW/mm2 irradiance for skin exposure within the American National Standard Institute (ANSI) limit. An example of a suitable commercially-available laser that can be implemented is the CL671-15 laser sold by CrystaLaser® of Reno Nev. When illuminating a skull, the returning photons from such illumination may carry information about the cerebral blood flow that can be used to infer the brain activity via neurovascular coupling as discussed in Lou, H. C., Edvinsson, L., MacKenzie, E. T., "The concept of coupling blood flow to brain function," Ann. Neurol. 22, 289-297 (1987) and Dirnagl, U., Niwa, K., Lindauer, U., Villringer, A., "Coupling of cerebral blood flow to neuronal activation: Role of adenosine and nitric oxide," Am. J. Physiol.-Hear. Circ. Physiol. 267 (1994), which are hereby incorporated by reference in their entireties.

Returning to FIG. 7, the iSVS system 700 include one or more lasers 710 that generate a laser beam, a first optical system 720 that splits the laser beam into a reference beam and a sample beam, and a fourth optical system 750. The fourth optical system 750 is at least in part configured or configurable to collect light from the reference arm and generate an off-axis reference beam incident on the one or more cameras 770 at an oblique angle θ (also referred to herein as the "tilt angle"). The fourth optical system 750 includes one or more optical components (e.g., one or more of a beam splitter, a lens, an optical fiber, mirror, etc.). In one aspect, the fourth optical system 750 includes an optical fiber for spatial filtering such as a single mode fiber. An example of a single mode fiber that can be used is a FB1, Thorlabs, PM460-HP made by Thorlabs. In one aspect, the tilt angle is in a range of several degrees. The tilt angle is designed based on the maximum spatial frequency bandwidth of the camera (determined by the pixel pitch) to ensure that no aliasing occurs.

According to one aspect, fourth optical system 750 includes one or more components configured to provide a tilt angle of the reference beam in order to position the off-axis of the sample speckle pattern so that the off-axis lobes containing sample data fit on the sides of the spatial frequency spectrum without overlapping with the other portion. The angle is chosen along with the size of the aperture to ensure that the off-axis lobes do not overlap with the sample autocorrelation term and also do not cause any aliasing.

During an image acquisition operation of the iSVS system 700, an off-axis reference beam interferes with scattered light from the sample 20 at the one or more sensors of the camera(s) 710 and the camera(s) records one or more interferograms. In one aspect, one or more interferograms are recorded during one exposure time. In another aspect, one or more interferograms are recorded during one or more respective exposure times. The camera may include one or more image sensors. Some examples of suitable image sensors are CMOS sensors, a charge-coupled device (CCD), and other similar devices. In one example, the sampling rate of the camera used is determined by the device properties, where typical sensors can have sampling rates up to ~HMz level. In one implementation, camera is set to have an exposure time in the range of about one to three order of magnitude longer than the decorrelation time. In typical blood flow measurement, the exposure time is set from several milliseconds to hundreds of milliseconds. In another implementation, depending on the dynamic properties of the measured object, the camera is set to have an exposure time in the range of about microsecond to about several seconds, depending on the common device specifications. Each interferogram is recorded during an exposure time.

Returning to FIG. 7, the iSVS system 700 includes a computing system 780 having one or more processors or other circuitry 782 and an internal non-transitory computer readable media (CRM) 784 in electrical communication with the processor(s) or other circuitry 782. The image data output from the one or more cameras 770 is transmitted (or "sent" or "communicated") in a signal to one or more processors or other circuitry 782 of the computing system 780. The computing system 780 is in electrical communication with the one or more cameras 770 to send control signals for controlling operations of the one or more cameras 770 and/or to receive one or more signals with image data such as one or more interferograms. The computing system 780 is optionally (denoted by dotted line) in electrical communication with the at least one laser 710 to send one or more control signals for controlling operations. The computing system 780 includes one or more processors or other circuitry 782 and an internal non-transitory computer readable medium 784 (e.g., memory) in electrical communication with the one or more processors 782.

The processor(s) or other circuitry of the computing system of the iSVS system 700 and, additionally or alternatively, other external processor(s) (e.g., a processor of the external computing system 789) can execute instructions stored on non-transitory computer readable media (e.g., internal non-transitory CRM 784 or optional external memory 792) to perform operations of the iSVS system 700. For example, the processor(s) or other circuitry may execute instructions to perform operations of an iSVS method to process the interferograms to determine a decorrelation time of the sample being imaged and/or determine a movement speed of an object in the sample. As another example, the processor(s) or other circuitry may send control signals to activate the laser(s) 710 and/or may send control signals to activate the camera(s) 770 to record during one or more exposure times to record one or more interferograms during image acquisition.

According to certain implementations, the computing system of an iSVS system can perform parallel image processing. To perform parallel image processing, the computing device generally includes at least one processor (or "processing unit"). Examples of processors include, for example, one or more of a general purpose processor (CPU), an application-specific integrated circuit, an programmable logic device (PLD) such as a field-programmable gate array (FPGA), or a System-on-Chip (SoC) that includes one or more of a CPU, application-specific integrated circuit, PLD as well as a memory and various interfaces.

The computing system of an iSVS system may be in communication with internal memory device and/or an external memory device. The internal memory device can include a non-volatile memory array for storing processor-executable code (or "instructions") that is retrieved by one or more processors to perform various functions or operations described herein for carrying out various logic or other operations on the image data. The internal memory device also can store raw image data, processed image data, and/or other data. In some implementations, the internal memory device or a separate memory device can additionally or alternatively include a volatile memory array for temporarily storing code to be executed as well as image data to be processed, stored, or displayed. In some implementations, the computing system itself can include volatile and in some instances also non-volatile memory.

Returning to FIG. 7, optionally (denoted by dotted lines) the iSVS system 700 includes a communication interface 785 and a display 786 in communication with the communication interface 785. The computing system 780 may be configured or configurable to output raw data, processed data such as image data, and/or other data over the communication interface 785 for display on the display 786. Optionally (denoted by dashed lines), the iSVS system 800 may further include one or more of a communication interface 787 and an external computing system 789 in communication with the communication interface 787, a communication interface 790 and an external memory device 792 in communication with the communication interface 790 for optional storage of data to the external memory device 792, and/or a communication interface 793 in communication with a user interface 794 for receiving input from an operator of the iSVS system 800. The optional user interface 794 is in electrical communication with the iSVS system 800 through the communication interface 793 to be able to send a control signal to the computing system 780 based on input received at the user interface 794.

In some implementations, the iSVS system includes a computing system configured or configurable (e.g., by a user) to: (i) output raw data, processed data such as image data, and/or other data over a communication interface to a display, (ii) output raw image data as well as processed image data and other processed data over a communication interface to an external computing device or system, (iii) output raw image data as well as processed image data and other data over a communication interface for storage in an external memory device or system, and/or (iv) output raw image data as well as processed image data over a network communication interface for communication over an external network (for example, a wired or wireless network). Indeed in some implementations, one or more of operations of an iSVS method can be performed by an external computing device. The computing system may also include a network communication interface that can be used to receive information such as software or firmware updates or other data for download by the computing device. In some implementations, an iSVS system further includes one or more other interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that one or more of components of the iSVS system can be electrically coupled to communicate with the computing device over one or more of a variety of suitable interfaces and cables such as, for example, USB interfaces and cables, ribbon cables, Ethernet cables, among other suitable interfaces and cables.

The described electrical communication between components of iSVS systems may be able to provide power and/or communicate data. The electrical communication between components of the iSVS systems described herein may be in wired form and/or wireless form.

Figure 8A:
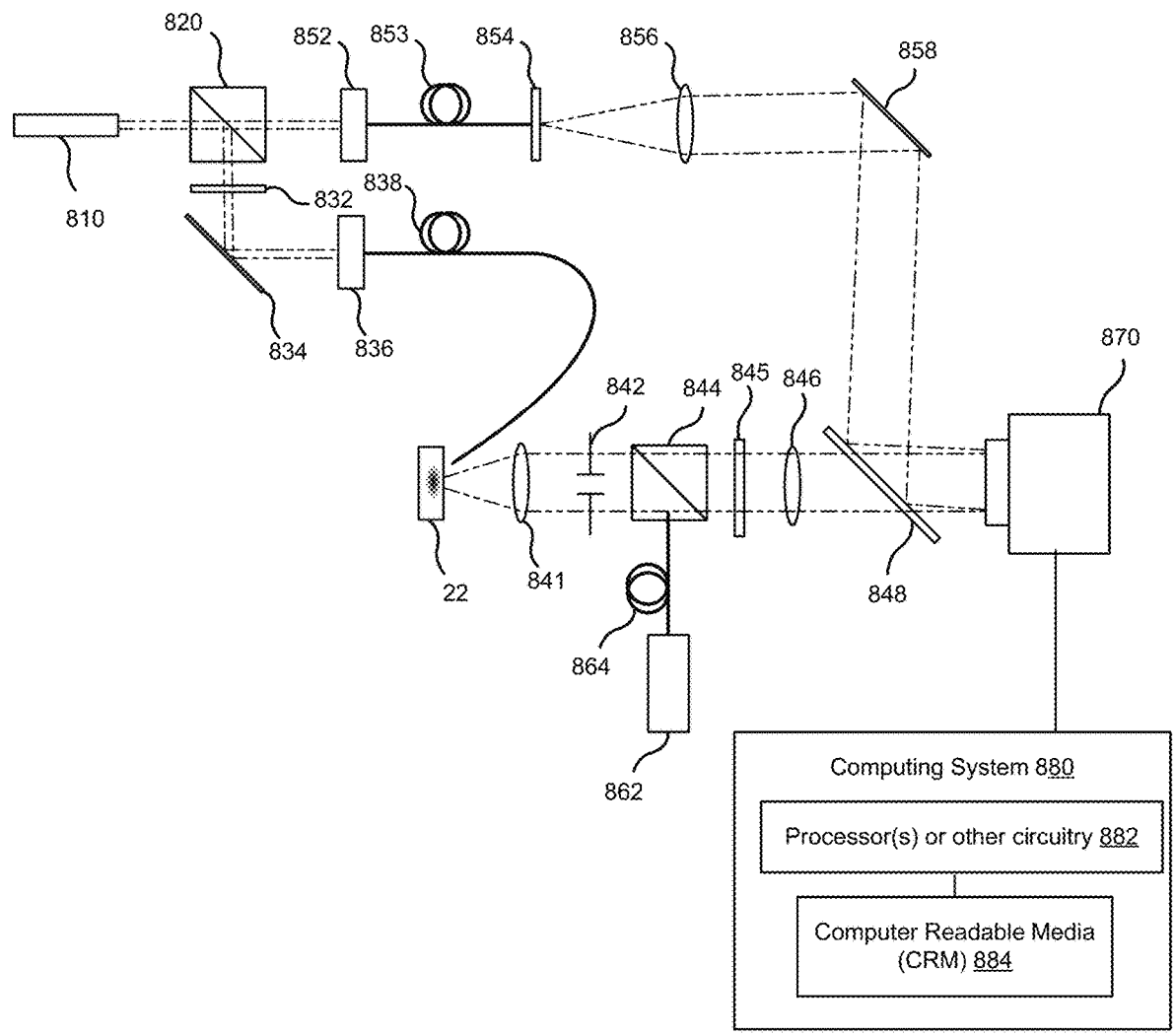
FIG. 8A is a schematic diagram of components of an iSVS system 800 in reflection mode, according to one implementation.

FIG. 8A is a schematic diagram of components of an iSVS system 800, according to one implementation. The iSVS system 800 is in an off-axis holographic configuration. The illustrated example is shown at an instant in time during an image acquisition while the sample 22 is being illuminated and imaged in reflection mode. During other operations, the sample 22 may not be present. The iSVS system 800 includes a laser 810 (e.g., a 532 nm, diode-pumped solid-state, long coherence length, laser) configured to provide a laser beam and a first optical system including a first beam splitter 820 configured to split the laser beam into a sample arm (also referred to herein as a "sample beam") and a reference arm (also referred to herein as a "reference beam"). In one example, the first beam splitter 820 is a polarizing beam splitter that is configured to reflect a first component of the laser beam with a particular polarization direction (e.g. 0 degrees) while transmitting a second component of the laser beam with a perpendicular polarization direction (e.g. 90 degrees). A half-wave plate 832 (Thorlabs WPH05M-532) is used to rotate the polarization of the deflected beam to match the polarization of the transmitted beam. An example of a commercially-available polarizing beam splitter is the polarizing beam splitter PBS251 from Thorlabs.

The iSVS system 800 also includes a second optical system that is at least in part configured or configurable collect and relay light from the sample beam to the sample 22 to illuminate the sample 22 being imaged. The second optical system includes a neutral-density filter 832 (Thorlabs NE10B) configured to filter light from the sample arm, a mirror 834 (Thorlabs PF10-03-G01) configured to reflect light, a first FP 836 (Thorlabs PAF2-A4A) configured to couple the light into the fiber 838 (Thorlabs P1-460B-FC-5), and a single mode fiber 838 (Thorlabs P1-460B-FC-5) coupled to the sample arm to direct the sample beam to the sample 22 to illuminate it. The neutral-density filters enable control of the laser intensity and the single mode fiber provides spatial filtering of the sample beam and enables it to be flexibly routed to the sample.

The iSVS system 800 also includes a third optical system that is at least in part configured or configurable to collect scattered light from the sample and image onto the camera 870 with a 4-f imaging system. The third optical system includes a first collection lens 841, an aperture 842 (e.g., a vertical slit) at the Fourier plane of the camera 870 to spatially filter the sample beam, a second beam splitter 844, a polarizer 845, a second lens 846, and a third beam splitter 848 (e.g., a plate beam splitter). The first lens 841 (e.g., a lens having a focal length of 60 mm) and the second lens 846 (e.g., a lens having a focal length of 200 mm) are in a 4-f optical configuration. The collection lens 841 is configured to collect light scattered by the sample 22 while being illuminated. The polarizer 845 is configured to filter scattered sample light out that does not share the same polarization as the reference beam. The third beam splitter 848 is configured to pass the scattered sample light and/or block light of other wavelength. The third optical system is configured to collect scattered light from the sample and image onto the camera 870 after being spatially filtered by the aperture 842 of the 4-f optical configuration.

The iSVS system 800 also includes a fourth optical system that is at least in part configured or configurable to collect light from the reference arm and generate an off-axis reference beam incident on the camera 870 at a tilt angle θ. An example of a commercially-available camera that can be used is the S640 camera made by Phantom. The fourth optical system includes a second FP 852 configured to couple light to the optical fiber, an optical fiber 853 coupled to the reference arm, a diffuser 854 configured to diffuse the light, a collimating lens 856 configured to collimate the reference arm to generate a collimated plane wave beam, and a mirror 858 configured to reflect the collimated beam to the third beam splitter 848. In one example, the optical fiber 853 is a single mode optical fiber for spatial filtering. An example of a commercially-available single mode fiber that can be used is a FB1, Thorlabs, PM460-HP made by Thorlabs. The third beam splitter reflects the collimated reference beam at a tilt angle θ to the camera 870. The tilt angle θ is with respect to a normal axis at the plane of the camera 870. The scattered light from the sample 22 is interfered with by the collimated, tilted reference beam on the camera 870. In one aspect, the tilt angle is in a range of about 0 rad to about 0.1 rad. In another aspect, the tilt angle is in a range of about 0 degree to about 5.7 degrees.

The iSVS system 800 also includes a computing system 880 having one or more processors or other circuitry 882 and an internal non-transitory computer readable media (CRM) 884 in electrical communication with the processor(s) or other circuitry 882.

The processor(s) or other circuitry 882, additionally or alternatively, other external processor(s), can execute instructions stored on memory such as internal non-transitory CRM 884 to perform operations of the iSVS system 800. For example, the processor(s) or other circuitry 882 may execute instructions to perform operations of an iSVS method to process the interferograms to determine a decorrelation time of the sample being imaged and/or determine a movement speed of an object in the sample. In addition or alternatively, the processor(s) or other circuitry may send control signals to activate the laser(s) 810 and/or may send control signals to activate the camera(s) 870 to record during one or more exposure times to record one or more interferograms during image acquisition.

The iSVS system 800 also includes a single photon counting module 862 and a single mode fiber 864 coupled to the single photon counting module 862. The single photon counting module 862 may be implemented to capture conventional DCS measurements of the sample dynamics for calibration of the iSVS system 800. The single photon counting module 862 and single mode fiber 864 may be removed when calibration is not in process.

Figure 8B:
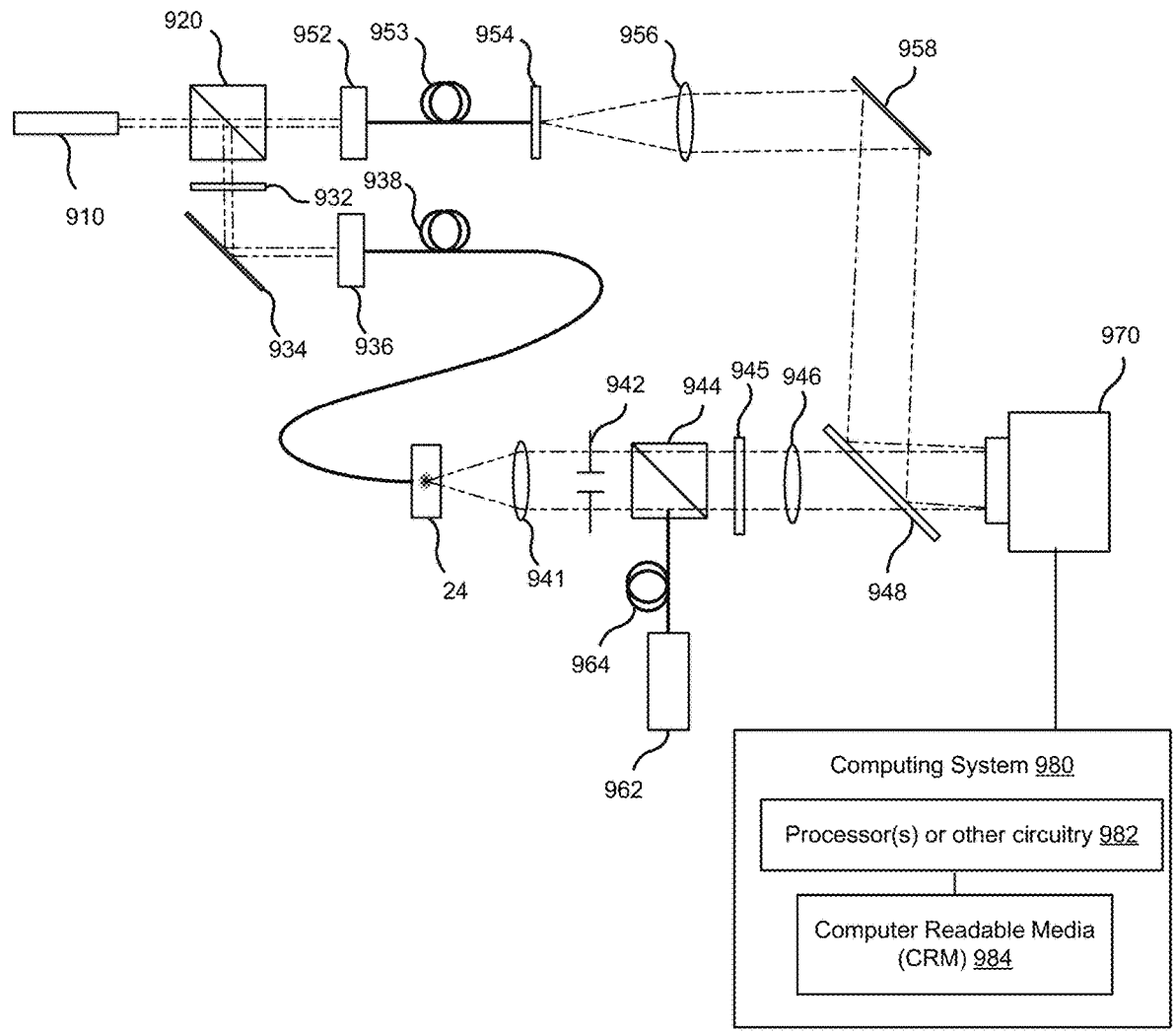
FIG. 8B is a schematic diagram of components of an iSVS system 900 in transmission mode, according to certain implementations

FIG. 8B is a schematic diagram of components of an iSVS system 900, according to certain implementations. The iSVS system 900 is in an off-axis holographic configuration. The illustrated example is shown at an instant in time during an image acquisition while the sample 24 is being illuminated and imaged in transmission mode. During other operations, the sample 24 may not be present. The iSVS system 900 includes a laser 910 (e.g., a 532 nm, diode-pumped solid-state, long coherence length, laser) configured to provide a laser beam and a first optical system including a first beam splitter 920 configured to split the laser beam into a sample arm (also referred to herein as a "sample beam") and a reference arm (also referred to herein as a "reference beam"). In one example, the first beam splitter 920 is a polarizing beam splitter that is configured to reflect a first component of the laser beam with a particular polarization direction (e.g., 0 degrees) while transmitting a second component of the laser beam with a perpendicular polarization direction (e.g., 90 degrees). An example of a commercially-available polarizing beam splitter is the polarizing beam splitter PBS251 from Thorlabs. A half-wave plate 832 (Thorlabs WPH05M-532) is used to rotate the polarization of the deflected beam to match the polarization of the transmitted beam.

The iSVS system 900 also includes a second optical system that is at least in part configured or configurable collect and relay light from the sample beam to the sample 24 to illuminate the sample 24 being imaged. The second optical system includes a neutral-density filter 832 (Thorlabs NE10B) configured to filter light from the sample arm, a mirror 834 (Thorlabs PF10-03-G01) configured to reflect light, a first FP 836 (Thorlabs PAF2-A4A) configured to couple light into the fiber, and a single mode fiber 838 (Thorlabs P1-460B-FC-5) coupled to the sample arm to direct the sample beam to the sample 24 to illuminate it.

The iSVS system 900 also includes a third optical system that is at least in part configured or configurable to collect scattered light from the sample in through transmission and image onto the camera 970 with a 4-f imaging system. The third optical system includes a first collection lens 941, an aperture 942 (e.g., a vertical slit) at the Fourier plane of the camera 970 to spatially filter the sample beam, a second beam splitter 944, a polarizer 945, a second lens 946, and a third beam splitter 948 (e.g., a plate beam splitter). The first lens 941 (e.g., a lens having a focal length of 60 mm) and the second lens 946 (e.g., a lens having a focal length of 200 mm) are in a 4-f optical configuration. The collection lens 941 is configured to collect light scattered by the sample 24 while being illuminated. The polarizer 945 is configured to filter scattered sample light out that does not share the same polarization as the reference beam. The third beam splitter 948 is configured to pass the scattered sample light and/or block light of other wavelength. The third optical system is configured to collect scattered light from the sample and image onto the camera 970 after being spatially filtered by the aperture 942 of the 4-f optical configuration.

The iSVS system 900 also includes a fourth optical system that is at least in part configured or configurable to collect light from the reference arm and generate an off-axis reference beam incident on the camera 970 at a tilt angle θ. An example of a commercially-available camera that can be used is the S640 camera made by Phantom. The fourth optical system includes a second FP 952 (Thorlabs PAF2-A4A) configured to couple light to the optical fiber, an optical fiber 953 (Thorlabs P1-460B-FC-5) coupled to the reference arm, a diffuser 954 (Thorlabs DG05-1500) configured to diffuse the light, a collimating lens 956 (Thorlabs, LA1024) configured to collimate the reference arm to generate a collimated plane wave reference beam, and a mirror 958 (Thorlabs PF10-03-G01) configured to reflect the collimated beam to the third beam splitter 948 (Thorlabs BSW25). In one example, the optical fiber 953 (Thorlabs P1-460B-FC-5) is a single mode optical fiber for spatial filtering. An example of a commercially-available single mode fiber that can be used is a FB1, Thorlabs, PM460-HP made by Thorlabs. The third beam splitter reflects the collimated reference beam at a tilt angle θ to the camera 970 (Phantom S640). The tilt angle θ is with respect to a normal axis at the plane of the camera 970 (Phantom S640). The scattered light from the sample 24 is interfered with by the collimated, tilted reference beam on the camera 970 (Phantom S640). In one aspect, the tilt angle is in a range of about 0 rad to about 0.1 rad. In another aspect, the tilt angle is in a range of about 0 degree to about 5.7 degrees.

The iSVS system 900 also includes a computing system 980 having one or more processors or other circuitry 982 and an internal non-transitory computer readable media (CRM) 984 in electrical communication with the processor(s) or other circuitry 982. The processor(s) or other circuitry 982, additionally or alternatively, other external processor(s), can execute instructions stored on memory such as internal non-transitory CRM 984 to perform operations of the iSVS system 900. For example, the processor(s) or other circuitry 982 may execute instructions to perform operations of an iSVS method to process the interferograms to determine a decorrelation time of the sample being imaged and/or determine a movement speed of an object in the sample. In addition or alternatively, the processor(s) or other circuitry may send control signals to activate the laser(s) 910 and/or may send control signals to activate the camera(s) 970 to record during one or more exposure times to record one or more interferograms during image acquisition.

The iSVS system 900 also includes a single photon counting module 962 and a single mode fiber 964 coupled to the single photon counting module 962. The single photon counting module 962 may be implemented to capture conventional DCS measurements of the sample dynamics for calibration of the iSVS system 900. The single photon counting module 962 and single mode fiber 964 may be removed when calibration is not in process.

Examples of Aperture Configurations

In certain implementations described herein, the iSVS system includes an aperture (e.g., vertical slit) at the Fourier plane of its camera. The camera is configured to record one or more interferograms that are low-pass filtered images based on the size and shape of the aperture. Some examples of shapes of aperture that are used in various implementations include circular, oval, rectangular, of other geometrical shape. The aperture sets the shape of the sample spectrum in the spatial frequency domain. In one aspect, the aperture is designed to increase or maximize the spatial bandwidth of the collected sample signal.

The available bandwidth in the spatial frequency domain for off-axis holography can be expressed by the four terms in Eqn. 2. In the spatial frequency domain, these four terms form the following signals: (i) the sample autocorrelation which is a convolution of the sample with itself and therefore has a bandwidth of 2B where B is the signal bandwidth, (ii) the reference autocorrelation which is a sharply peaked delta-like function, and (iii) the two off-axis lobe terms which are the convolution of the sample with a shifted delta function from the tilted reference beam. To increase or maximize the bandwidth of the sample signal in the spatial frequency domain, an aperture may be selected to design the shape and size of the sample bandwidth such that the off-axis lobes may maximally or have an increased fit in the spatial frequency domain without the off-axis lobes with the sample autocorrelation term or aliasing.

In iSVS systems, the sample field is a speckle field and increasing or maximizing the number of speckles sampled is desired. A circular pupil leaves unused space in the spatial frequency domain around the circular pupil. To increase or maximize the number of speckle grains that are sampled, the iSVS systems, of certain implementations, are designed to have the speckle field cover an increased or maximum number of imaging pixels at the camera and to increase or maximize the spatial frequency bandwidth (smallest speckle size) allowable without aliasing. For example, in one aspect, an iSVS system implements a rectangular aperture in the Fourier plane to set the shape of the sample spectrum to increase the space in the spatial frequency domain. This iSVS system can then use the tilt angle of the reference beam to position the off-axis lobes so that they fit on the sides of the spatial frequency spectrum without overlapping with the other terms.

Figure 9A:
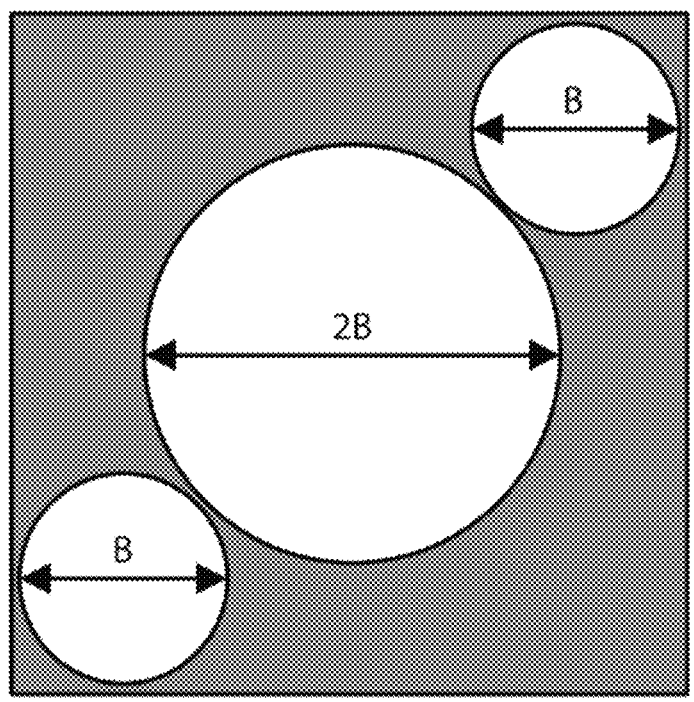
FIG. 9A is an illustration of an example of an off-axis holography spatial frequency spectrum with a circular sample bandwidth implemented by using a circular aperture at the Fourier plane of an iSVS system, according to an implementation.

FIG. 9A is an illustration of an example of an off-axis holography spatial frequency spectrum with a circular sample bandwidth implemented by using a circular aperture at the Fourier plane, according to an implementation. Using the circular aperture enables maintaining isotropic lateral resolution but may not efficiently use the information capacity of the system since there is unused space (shown shaded in gray) in the spatial frequency domain. The off-axis holography spatial frequency spectrum includes two off-axis lobes, each with a bandwidth of B and a central third lobe having a bandwidth of 2B where B is the sample signal bandwidth.

Figure 9B:
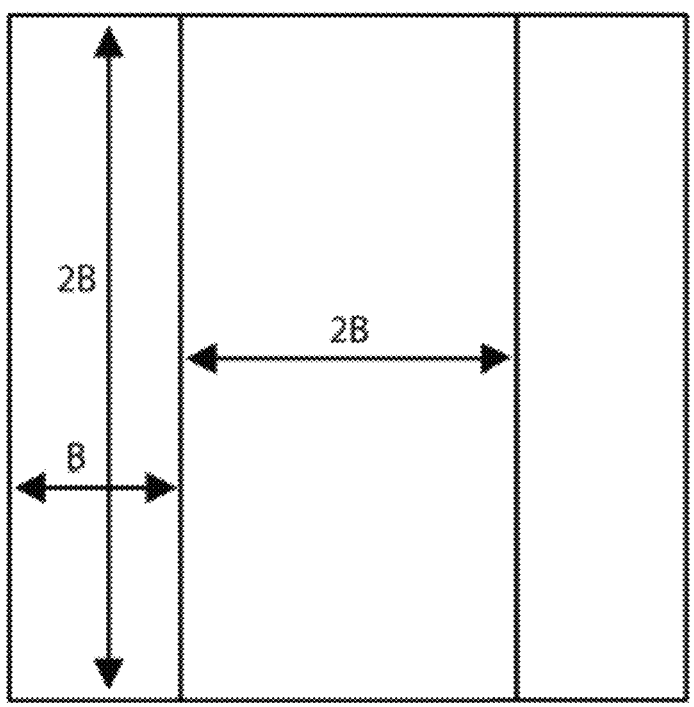
FIG. 9B is an illustration of an example of an off-axis holography spatial frequency spectrum with a rectangular sample bandwidth implemented by using a rectangular aperture at the Fourier plane of an iSVS system, according to an implementation

FIG. 9B is an illustration of an example of an off-axis holography spatial frequency spectrum with a rectangular sample bandwidth implemented by using a rectangular aperture at the Fourier plane, according to an implementation. By using the rectangular aperture to shape limit the spatial frequency content of the sample field, the spatial frequency domain can be fully used. The off-axis holography spatial frequency spectrum includes two off-axis lobes, each with a bandwidth of B and a central third lobe having a bandwidth of 2B where B is the sample signal bandwidth.

V. Examples of Results

Decorrelation Caused by Breathing and Blood Flow in Rodents

An iSVS system such as, e.g., the iSVS system 800 described with respect to FIG. 8, was used to measure the dynamic decorrelation caused by breathing and blood flow in a rat. The iSVS system was first calibrated using an iSVS calibration method such as the method described with respect to the flowchart shown in FIG. 6. During image acquisition, the iSVS system was used to illuminate the dorsal skin flap of the anesthetized rat in both transmission and reflection modes and a series of frames of off-axis interferograms were recorded by the camera. The iSVS system implemented an iSVS method such as, e.g., the method shown in FIG. 3, to process the series of off-axis interferograms to analyze the dynamic behavior of the captured light. For comparison, an SVS system was also used to image the dorsal skin flap of the anesthetized rat in both transmission and reflection modes.

FIGS. 13A, 14A, 15A, 16A, 17A, and 18A are graphs with plots of effective speckle visibility over time (seconds) for the dorsal skin flap as measured by the iSVS system in transmission mode (e.g., iSVS system 900 shown in FIG. 8B) where the laser powers were 1 mW, 0.5 mW, 0.26 mW, 0.13 mW, 0.06 mW, and 0.03 mW respectively, according to implementations. During operation, the camera of the iSVS system recorded a series of interferograms while the sample beam power was reduced in steps from 1 mW, 0.5 mW, 0.26 mW, 0.13 mW, 0.06 mW, and 0.03 mW.

FIGS. 13B, 14B, 15B, 16B, 17B, and 18B are graphs with plots of speckle contrast over time (seconds) for the dorsal skin flap as measured by an SVS system in transmission mode for comparison where the laser powers were 11 mW, 0.5 mW, 0.26 mW, 0.13 mW, 0.06 mW, and 0.03 mW respectively, according to implementations. During operation, the camera of the SVS system recorded a series of images while the sample beam power was reduced in steps from 1 mW, 0.5 mW, 0.26 mW, 0.13 mW, 0.06 mW, and 0.03 mW.

FIGS. 19A, 20A, 21A, 22A, 23A, and 24A are graphs with plots of effective speckle visibility over time (seconds) for the dorsal skin flap as measured by the iSVS system in reflection mode (e.g., iSVS system 800 shown in FIG. 8A) where the laser powers were 1 mW, 0.5 mW, 0.26 mW, 0.13 mW, 0.06 mW, and 0.03 mW respectively, according to implementations. During operation, the camera of the iSVS system recorded a series of interferograms while the sample beam power was reduced in steps from 1 mW, 0.5 mW, 0.26 mW, 0.13 mW, 0.06 mW, and 0.03 mW.

FIGS. 19B, 20B, 21B, 22B, 23B, and 24B are graphs with plots of speckle contrast over time (seconds) for the dorsal skin flap as measured by an SVS system in reflection mode for comparison where the laser powers were 1 mW, 0.5 mW, 0.26 mW, 0.13 mW, 0.06 mW, and 0.03 mW respectively, according to implementations. During operation, the camera of the SVS system recorded a series of images while the sample beam power was reduced in steps from 1 mW, 0.5 mW, 0.26 mW, 0.13 mW, 0.06 mW, and 0.03 mW.

Figure 17A:
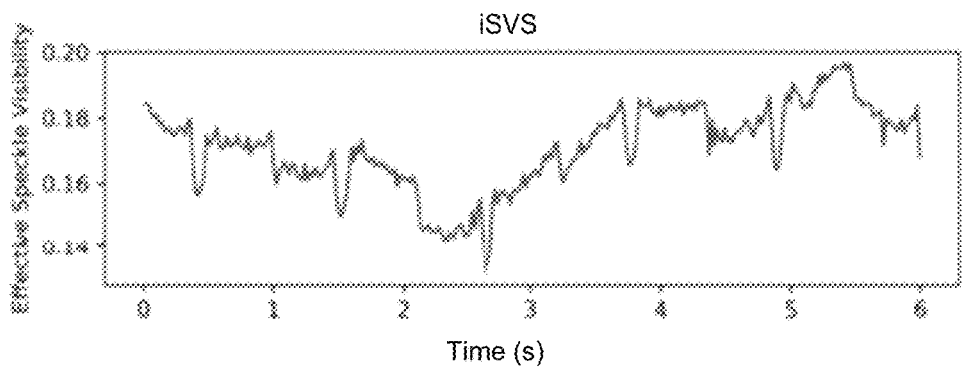
Figure 17B:
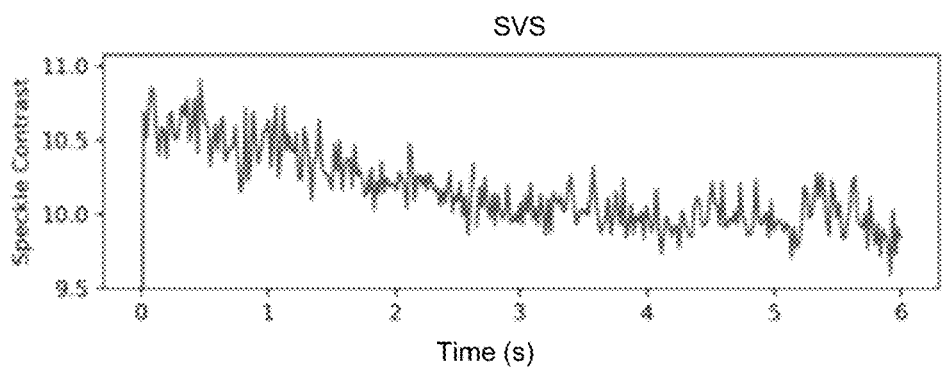
FIG. 17B is a graph with a plot of effective speckle visibility over time (seconds) for a dorsal skin flap as measured by an SVS system in transmission mode where the laser power was 0.06 mW, according to one example.
Figure 18A:
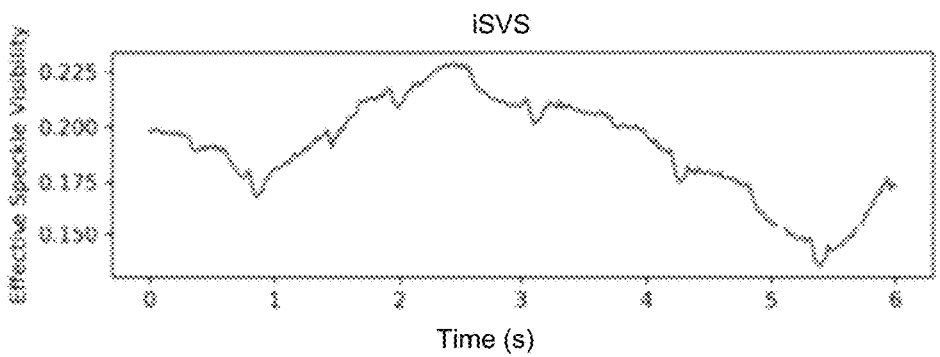
Figure 18B:
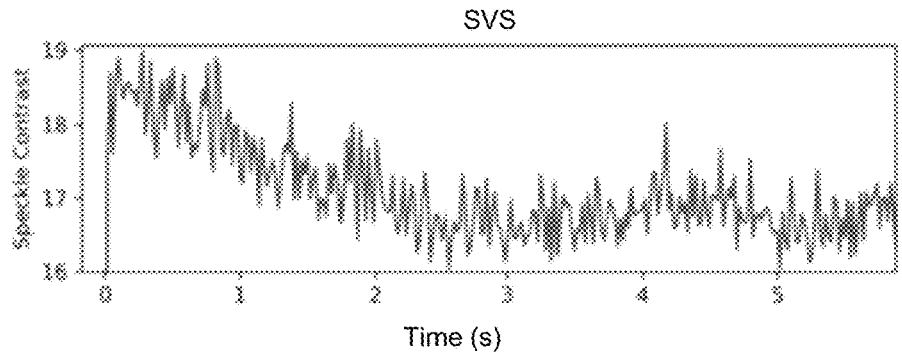
FIG. 18B is a graph with a plot of effective speckle visibility over time (seconds) for a dorsal skin flap as measured by an SVS system in transmission mode where the laser power was 0.03 mW, according to one example.
Figure 19A:
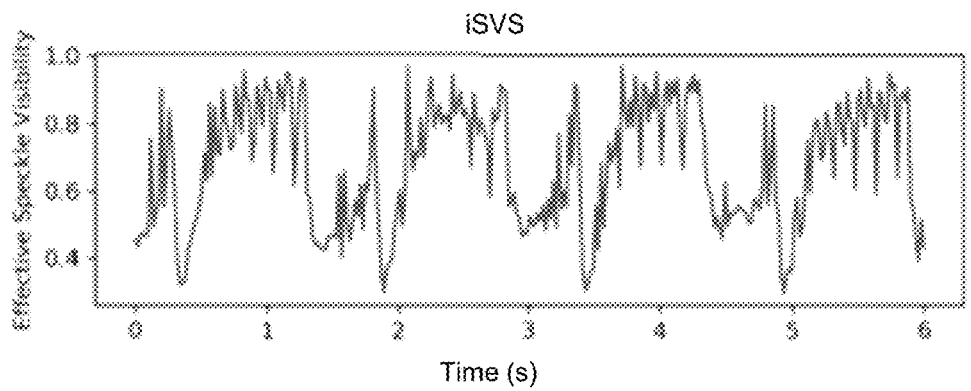
FIG. 19A is a graph with a plot of effective speckle visibility over time (seconds) for a dorsal skin flap as measured by an iSVS system in reflection mode where the laser power was 1.0 mW, according to one example.
Figure 19B:
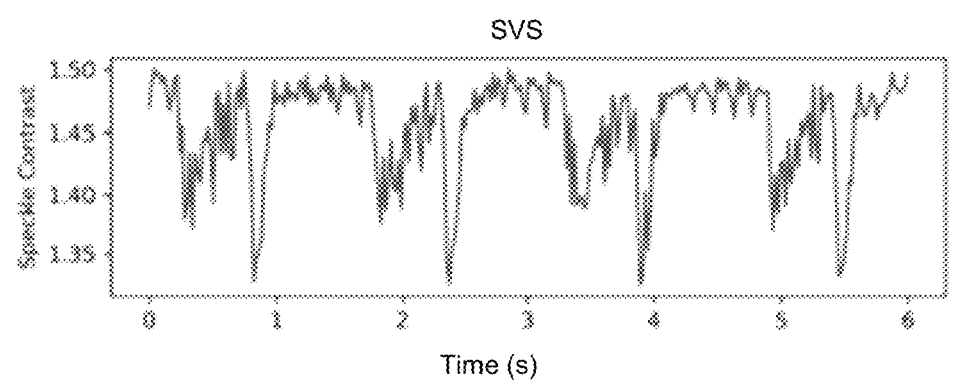
FIG. 19B is a graph with a plot of effective speckle visibility over time (seconds) for a dorsal skin flap as measured by an SVS system in reflection mode where the laser power was 1.0 mW, according to one example.
Figure 20A:
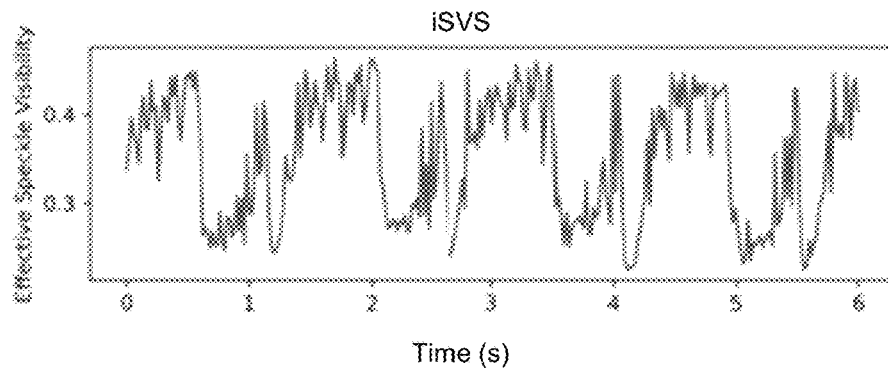
FIG. 20A is a graph with a plot of effective speckle visibility over time (seconds) for a dorsal skin flap as measured by an iSVS system in reflection mode where the laser power was 0.50 mW, according to one example.
Figure 20B:
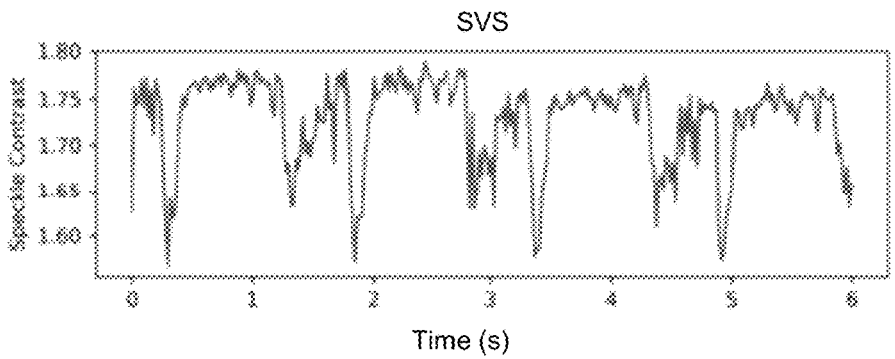
FIG. 20B is a graph with a plot of effective speckle visibility over time (seconds) for a dorsal skin flap as measured by an SVS system in reflection mode where the laser power was 1.0 mW, according to one example.
Figure 21A:
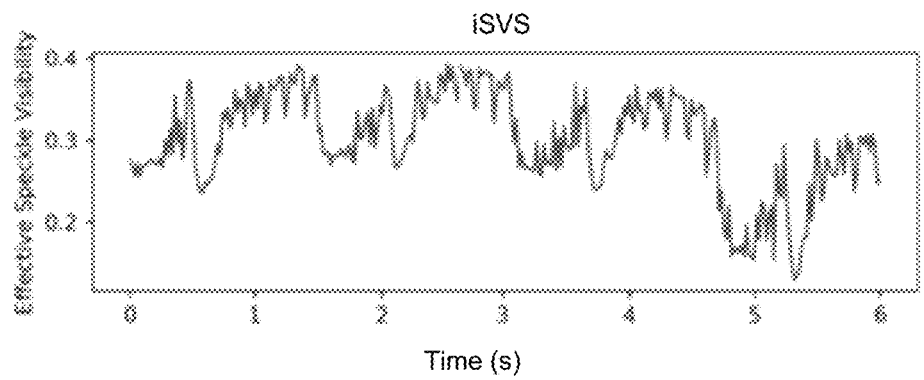
FIG. 21A is a graph with a plot of effective speckle visibility over time (seconds) for a dorsal skin flap as measured by an iSVS system in reflection mode where the laser power was 0.26 mW, according to one example.
Figure 21B:
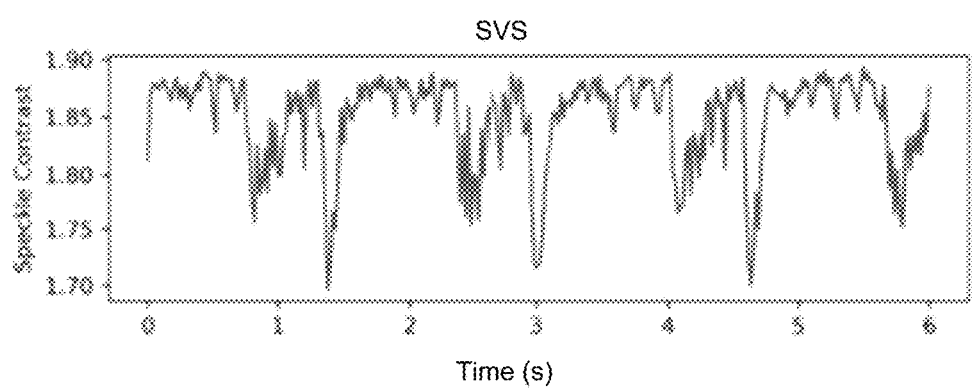
FIG. 21B is a graph with a plot of effective speckle visibility over time (seconds) for a dorsal skin flap as measured by an SVS system in reflection mode where the laser power was 0.26 mW, according to one example.
Figure 22A:
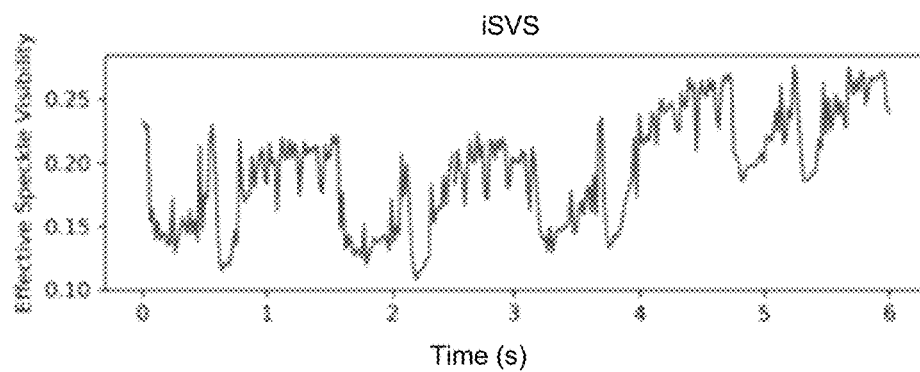
FIG. 22A is a graph with a plot of effective speckle visibility over time (seconds) for a dorsal skin flap as measured by an iSVS system in reflection mode where the laser power was 0.13 mW, according to one example.
Figure 22B:
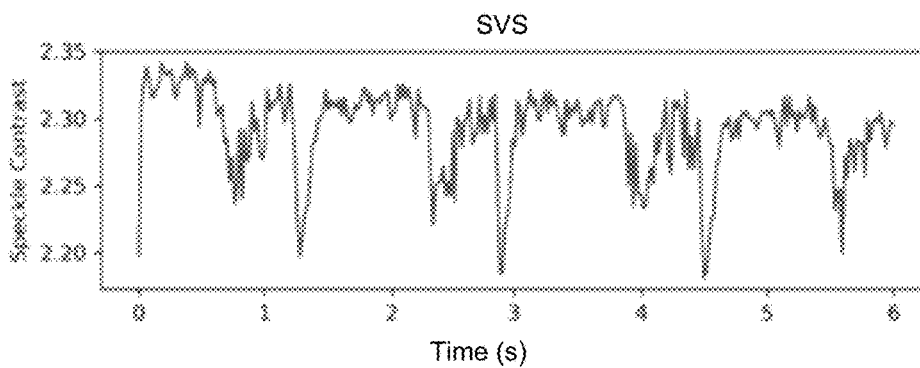
FIG. 22B is a graph with a plot of effective speckle visibility over time (seconds) for a dorsal skin flap as measured by an SVS system in reflection mode where the laser power was 0.13 mW, according to one example.
Figure 23A:
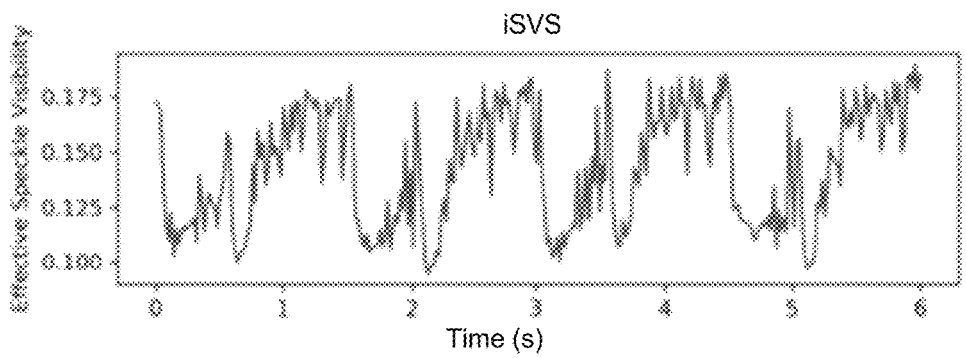
FIG. 23A is a graph with a plot of effective speckle visibility over time (seconds) for a dorsal skin flap as measured by an iSVS system in reflection mode where the laser power was 0.06 mW, according to one example.
Figure 23B:
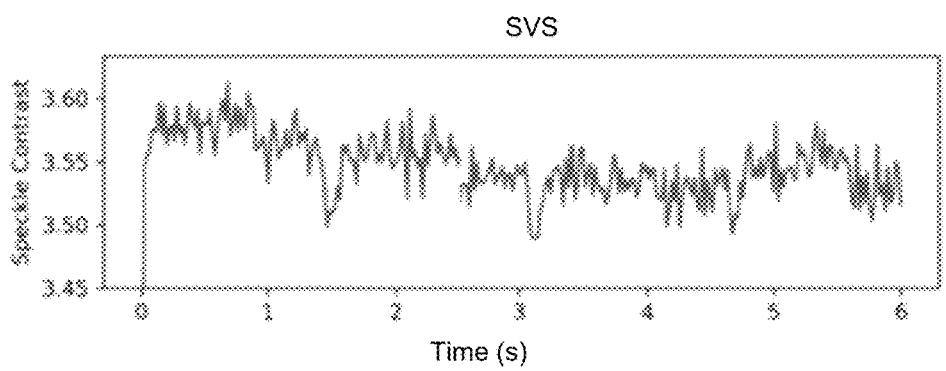
FIG. 23B is a graph with a plot of effective speckle visibility over time (seconds) for a dorsal skin flap as measured by an SVS system in reflection mode where the laser power was 0.06 mW, according to one example.
Figure 24A:
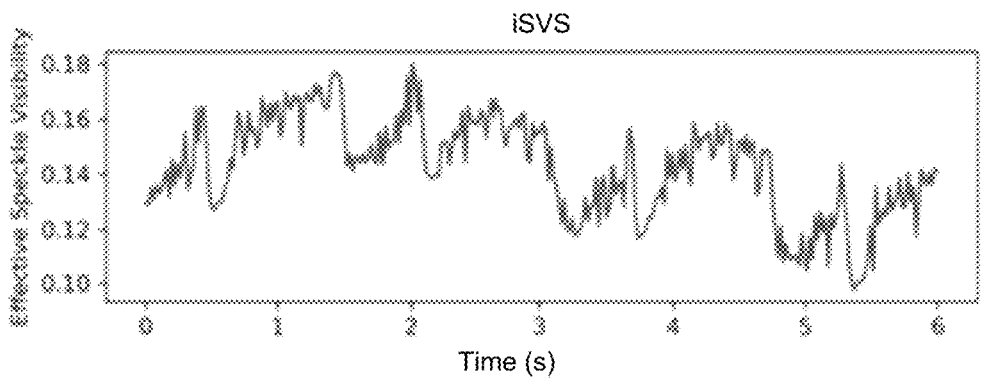
FIG. 24A is a graph with a plot of effective speckle visibility over time (seconds) for a dorsal skin flap as measured by an iSVS system in reflection mode where the laser power was 0.03 mW, according to one example.
Figure 24B:
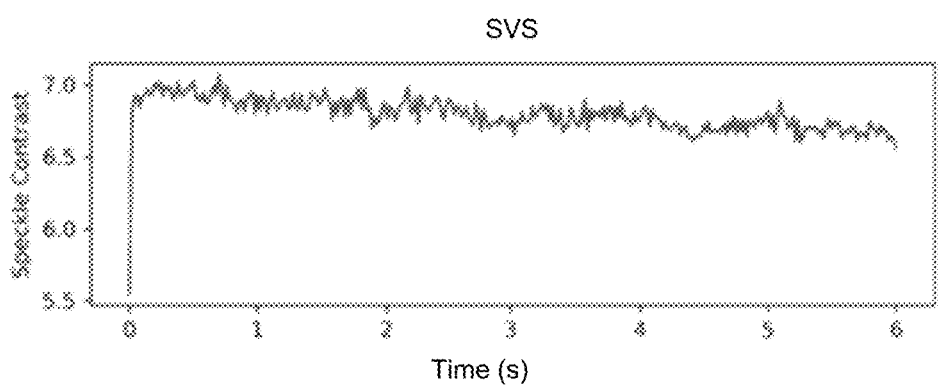
FIG. 24B is a graph with a plot of effective speckle visibility over time (seconds) for a dorsal skin flap as measured by an SVS system in reflection mode where the laser power was 0.03 mW, according to one example.

As can be seen in, for example, FIG. 17B, FIG. 18B, FIG. 23B, and FIG. 24B, when the signal light intensity drops to lower levels with laser power set at lower levels, the decorrelation signal with speckle contrast from the SVS system appears to be buried in camera noise, and the SVS system can no longer accurately detect decorrelation signal changes. Due to the heterodyne gain provided by the reference beam in the iSVS system, the iSVS system can detect the decorrelation signal due to breathing and even the blood flow from heat beating down to a sample laser beam power of 0.06 mW as shown in FIG. 17A for transmission mode and as shown in FIG. 23A for reflection mode. The iSVS system detected a decorrelation signal due to breathing that has a frequency of about $\frac{2}{3}$ Hz and a decorrelation signal due blood flow from heart beating that has a frequency of about 6 Hz. These frequencies are determined by analyzing the Fourier transform of the measured time traces and isolating the locations of peaks in the frequency spectrum.

In Vivo Measurement of Cerebral Blood Flow in Humans

Figure 25:
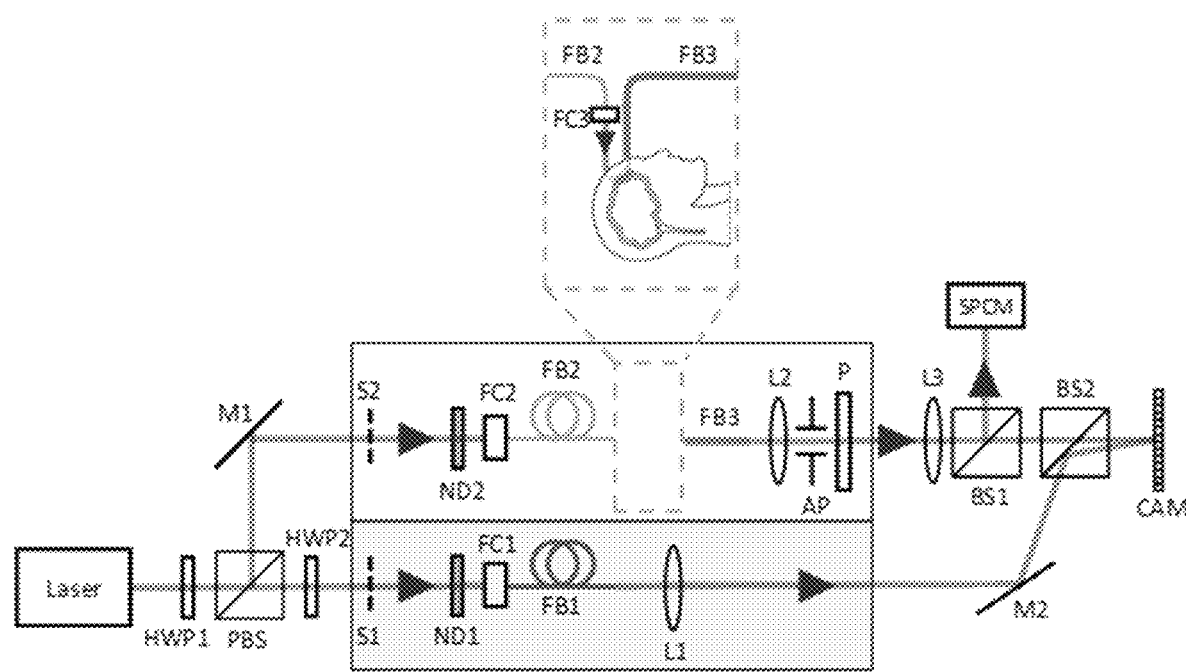
FIG. 25 is a schematic diagram of components of an iSVS system, according to an embodiment.

FIG. 25 is a schematic diagram of components of an iSVS system 2500, according to an embodiment. The iSVS system 2500 includes a first half wave plate labeled "HWP1," a plate beam splitter labeled "PBS," a second half wave plate labeled "HWP2," a first signal labeled "S1," a first neutral-density filter labeled "ND1," a first fiber coupler labeled "FC1" coupled to the first neutral-density filter ND1, a first fiber bundle labeled "FB 1" coupled to the first fiber coupler FCI, a first lens labeled "L1," a first mirror labeled "M1," and a second mirror labeled "M2," a second signal labeled "S2," a second neutral-density filter labeled "ND2," a second fiber coupler labeled "FC2" coupled to the second neutral-density filter ND2, a second fiber bundle labeled "FB2" coupled to the second fiber coupler FC2, a third fiber coupler labeled "FC3" coupled to the FB2, a third fiber bundle labeled "FB3" receiving scattered light from the human subject 26, a second lens labeled "L2," an aperture labeled "AP" at the Fourier plane of the camera, a polarizer labeled "P," a third lens labeled "L3," a first beam splitter labeled "BS1," a second beam splitter labeled "BS2," and a camera labeled "CAM." The iSVS system 2500 is shown during an image acquisition operation while a human subject 26 is being imaged. A single photon counting module (SPCM) is also included. The second beam splitter is included to split the light onto the single-photon-counting module for a calibration operation. Non-contact source and detector fibers coupled to the third fiber coupler FC3 were mounted above the human subject forehead over the prefrontal cortex area. The iSVS system 2500 also includes a laser configured to generate an illuminating laser beam such as a laser beam from a 671-nm laser source. In this example, the second fiber bundle FB2 is a multimode fiber such as, e.g., the commercially-available M31L02 multimode fiber sold by Thorlabs with ~3000 modes. The laser beam was coupled to the second fiber bundle FB2. In one example, a collimated 56 mW laser beam with a 6-mm spot size resulted in a <2 mW/mm$^2$ irradiance for skin exposure. The diffused light at various source-detector separations was collected by the third fiber bundle FB3. In one example, the third fiber bundle FB3 is a large core multimode fiber such as the commercially-available M107L02 large core multimode fiber sold by M107L02 with a core diameter of 1.5 mm and containing ~6 million modes. The output from the third fiber bundle FB3 was channeled through the sample arm of the interferometric setup where the diffused light and the reference beam are combined by the beam splitter and recorded by the camera.

Figure 26:
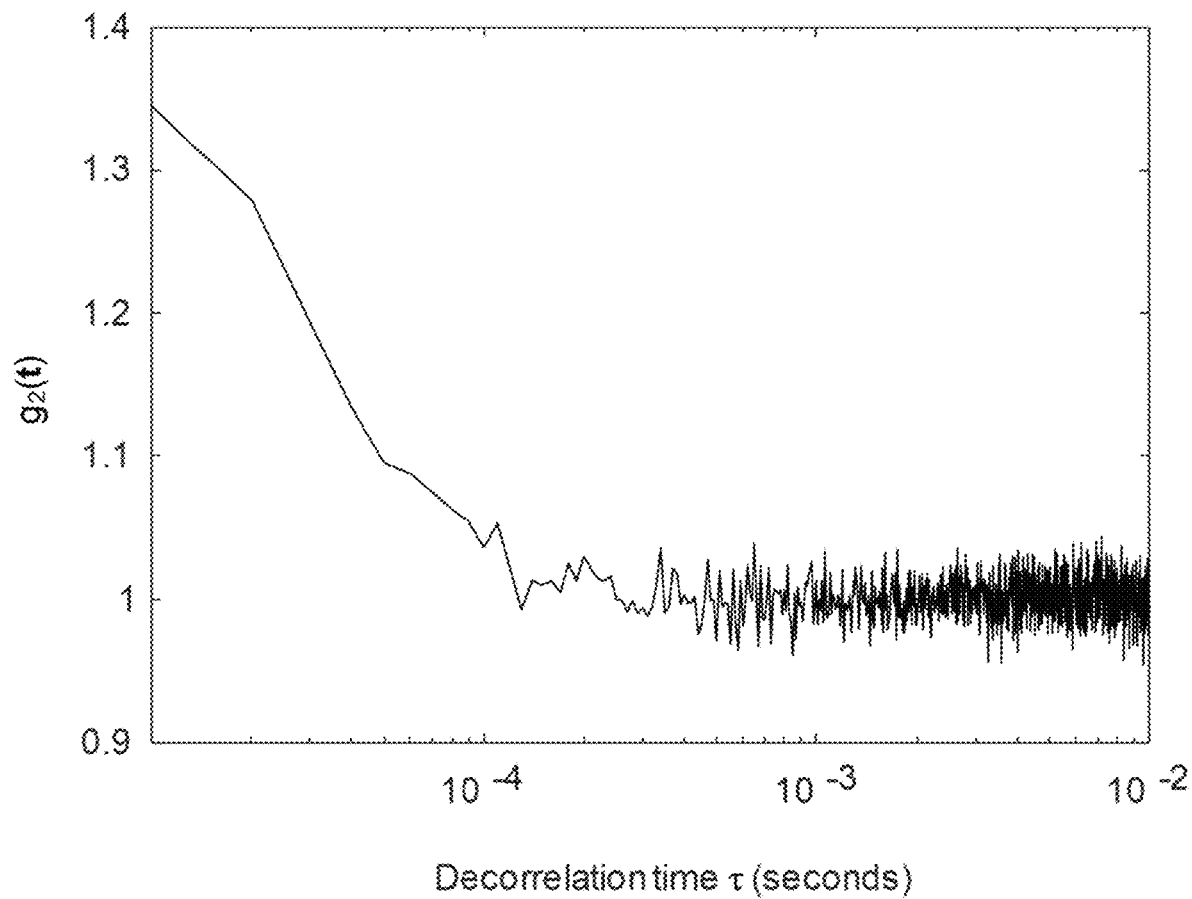
FIG. 26 is a graph of a plot of the intensity decorrelation curve g2(t) measured by the iSVS system shown in FIG. 25, according to an example.

The iSVS system 2500 was implemented to monitor the blood flow in humans when the reflected light signal was low. When the S-D separation was 1.5 cm, the photon count rate read by the SPCM was ~1500 counts/second, while the dark count rate of the SPCM was ~180 counts/second. The iSVS system 2500 took measurements used to generate the intensity decorrelation curve g2(t) shown in FIG. 26 based on a measurement time of 50 s. FIG. 26 is a graph of a plot of the intensity decorrelation curve g2(t) measured by the iSVS system 2500, according to an example. The decorrelation time is ~50 μs.

Figure 27:
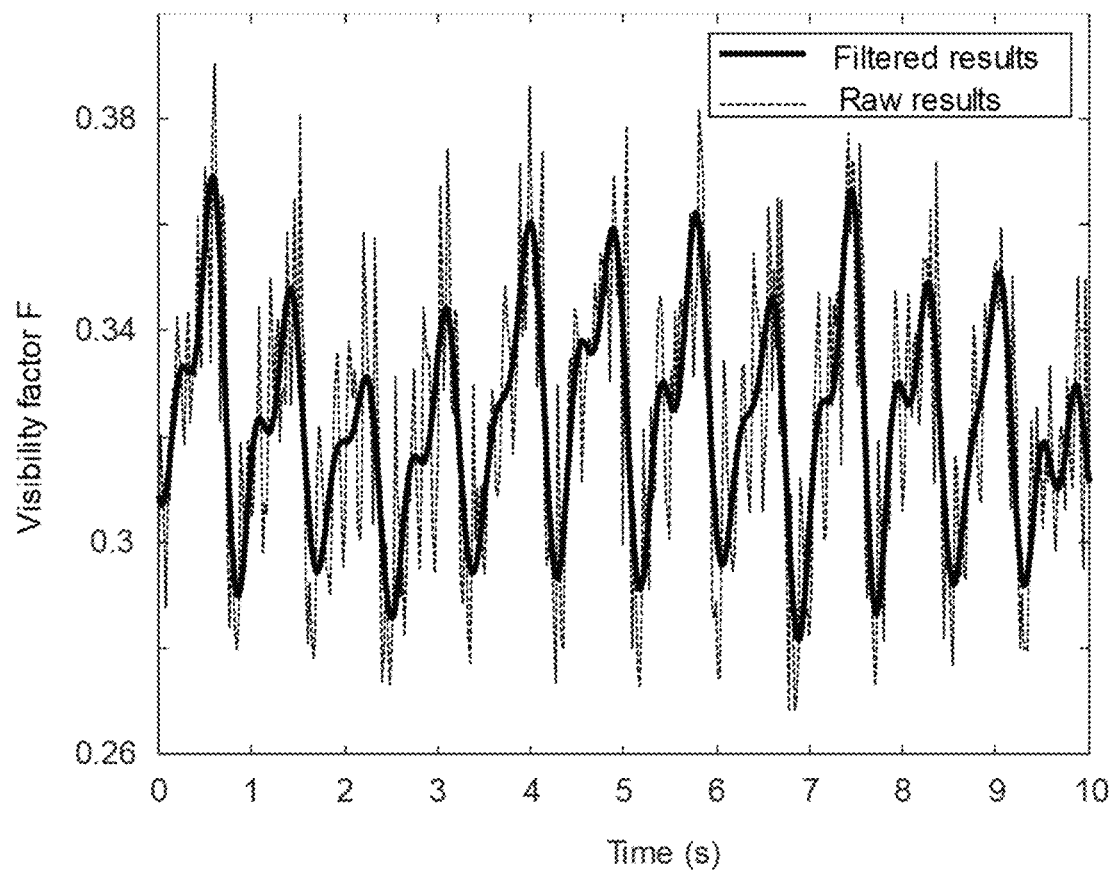
FIG. 27 is a graph of a plot of the visibility factors measured at 100 Hz on the forehead of a human subject using the iSVS system shown in FIG. 25, according to an example.

The ISVS system with a camera exposure time of 2 ms and an FPS of 100 Hz yielded a pulsatile signal trace, shown by the dotted line in FIG. 27. The filtered signal trace is the solid line in FIG. 27.

Figure 28:
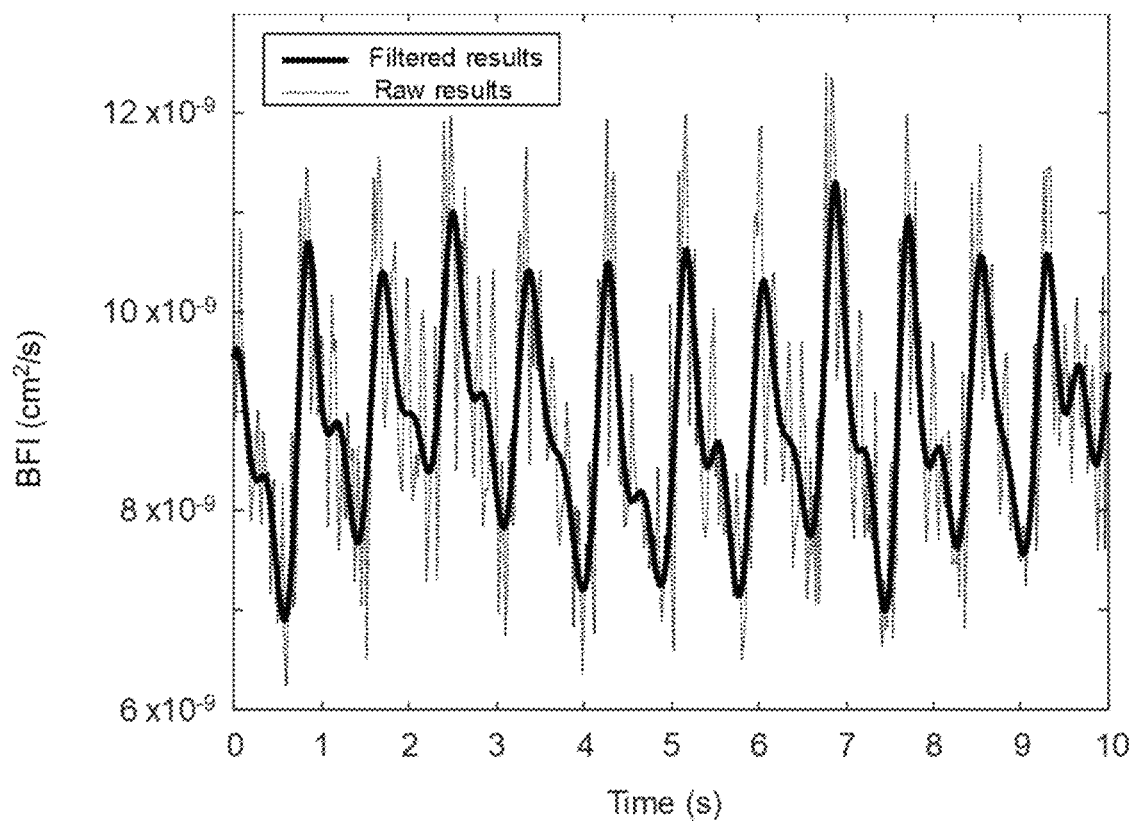
FIG. 28 is a graph of a plot of the blood flow index calculated from the visibility factors in FIG. 27, according to an example.
Figure 29:
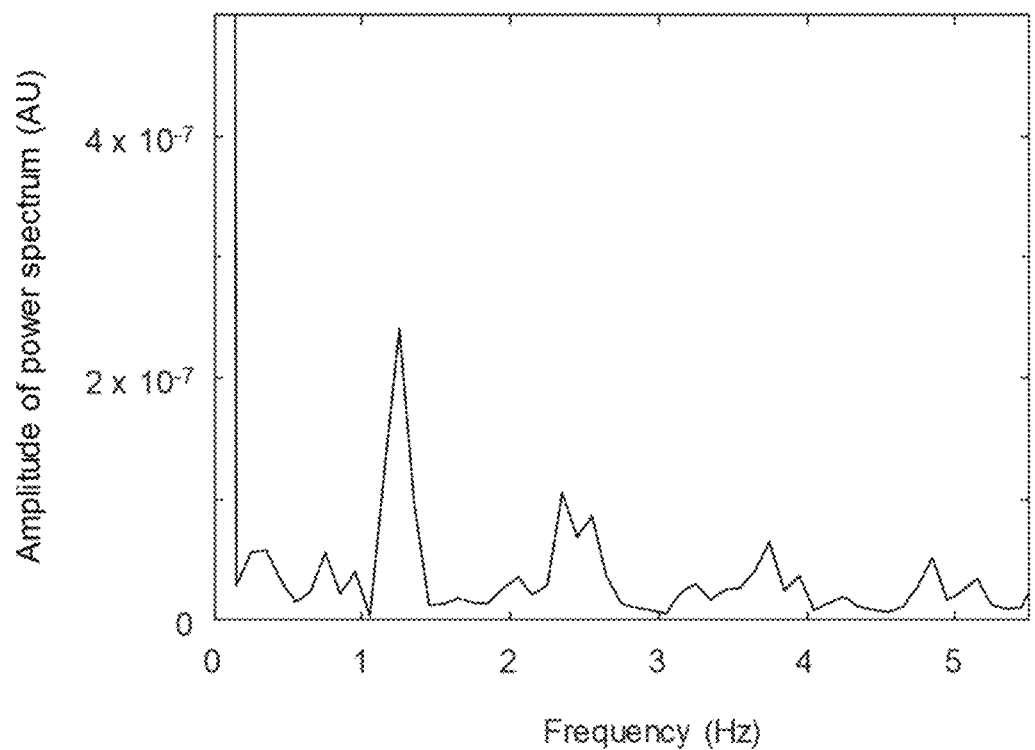
FIG. 29 is a graph of a plot of the Fourier transform of the curve shown in FIG. 28, according to an example.

The visibility factor measured by the ISVS system 2500 was used to calculate the blood flow index (BFI) based on the tissue scattering parameters used in Durduran, T., Choe, R., Baker, W. B., Yodh, A. G., "Diffuse optics for tissue monitoring and tomography," *Reports Prog. Phys.* 73 (2010), p. 76701, which is hereby incorporated by reference in its entirety. The raw and filtered BFI traces are presented in blue and red curves in FIG. 28, respectively. The Fourier transform of the raw BFI trace is shown in FIG. 29, and the heart-beat frequency ~1.1 Hz and its harmonics are highlighted. In this experimental configuration, the average photon electron number of the signal beam on each camera pixel was ~0.95, where the detector noise was ~1.2 photon electrons. In this case, the SNR for each pixel was ~0.79.

Figure 30:
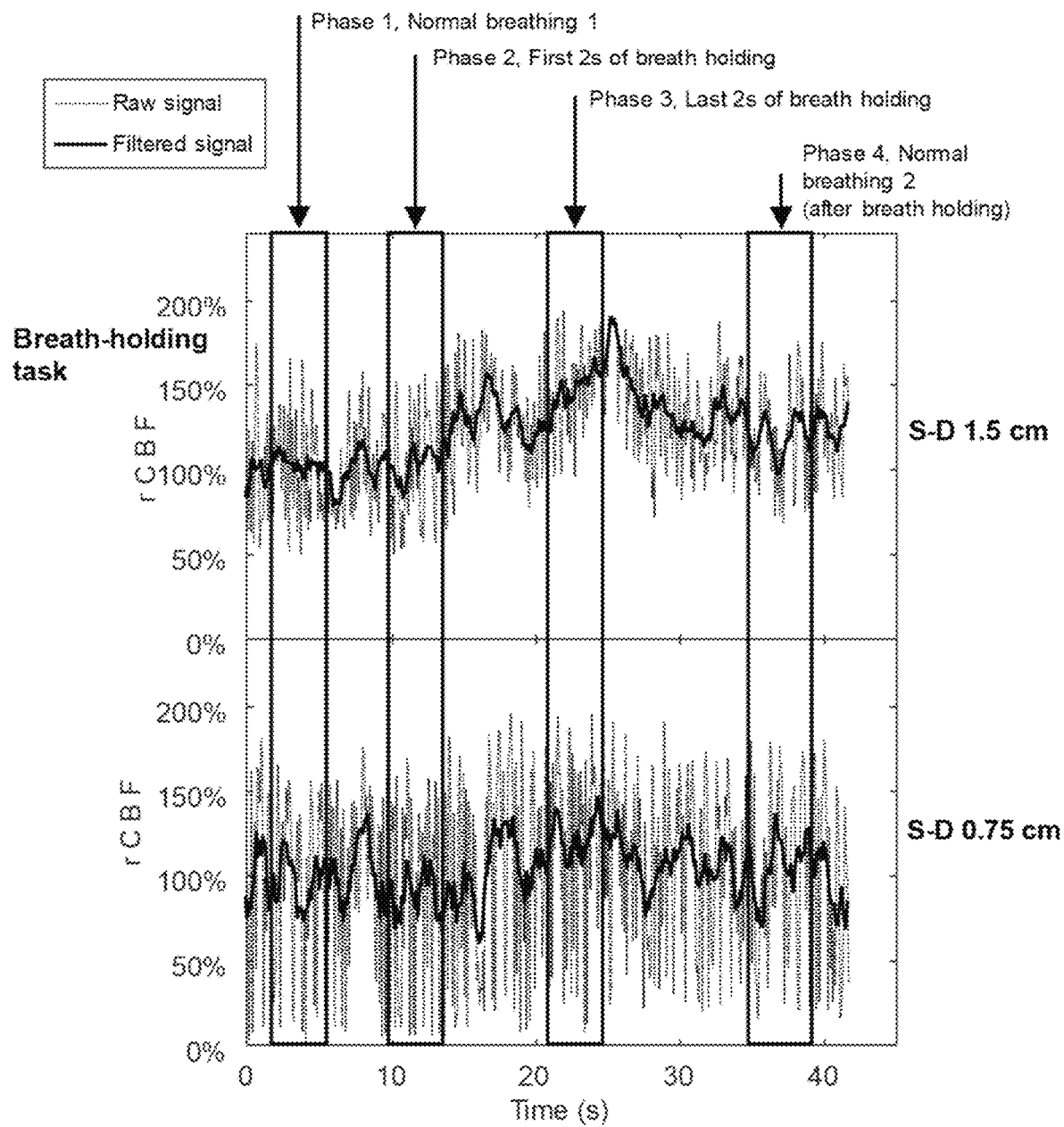
FIG. 30 is a graph of a plot of the heart beat frequency measured by an iSVS system, according to an example.
Figure 31:
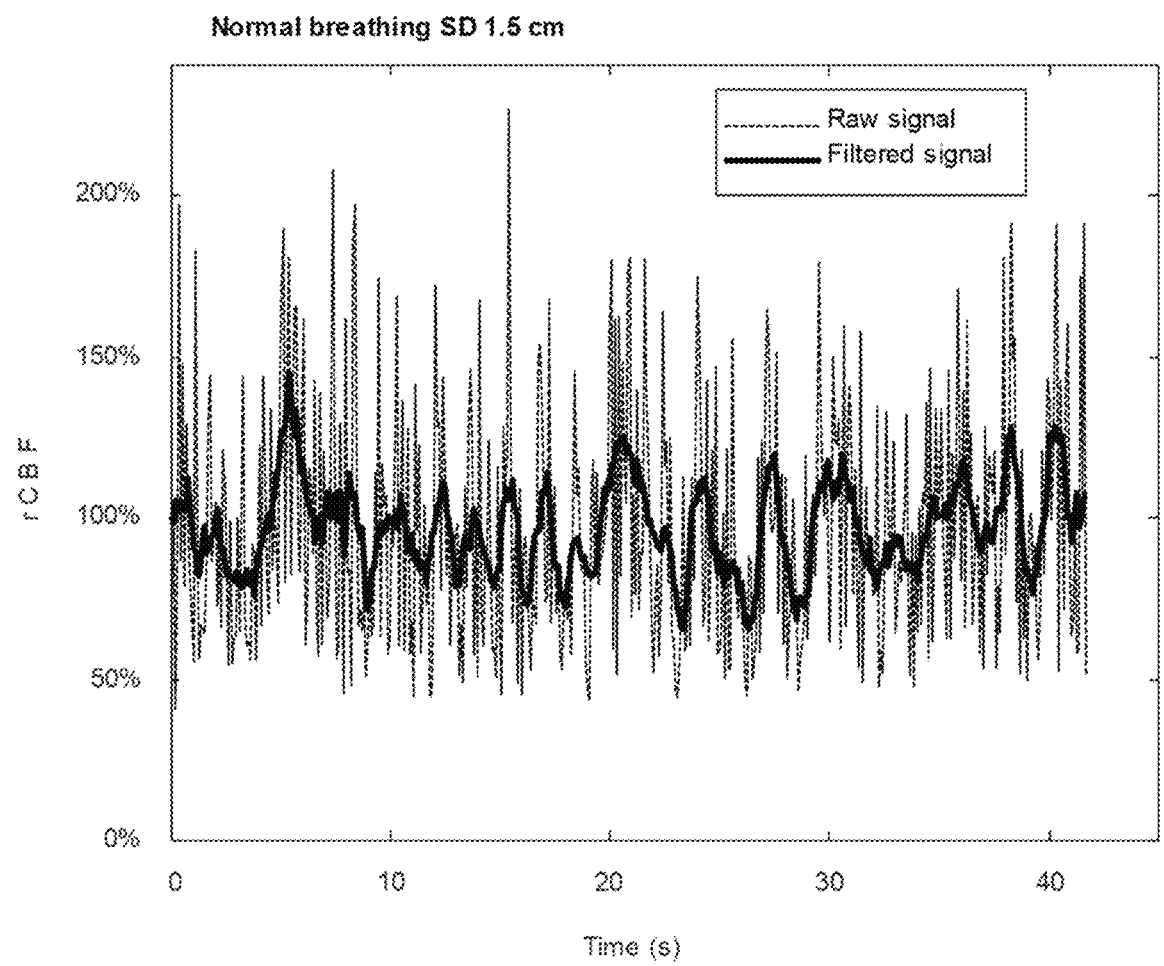
FIG. 31 is a graph of a plot of cerebral blood flow traces measured by an iSVS system when the human subject was holding breath, according to an example.

The iSVS system 2500 was used to take measurements for three cases: (i) An S-D separation of $d_1$=1.5 cm while the human subject 26 went through a breath-holding task, (ii) an S-D separation of $d_1$=0.75 cm while the human subject 26 went through a breath-holding task, and (iii) an S-D separation of $d_2$=1.5 cm while the human subject 26 breathed normally. The representative recorded traces for case (i), (ii) and (iii) are shown in FIG. 30 and FIG. 31, respectively. For each case, five repetitive experiments were conducted.

Figure 32:
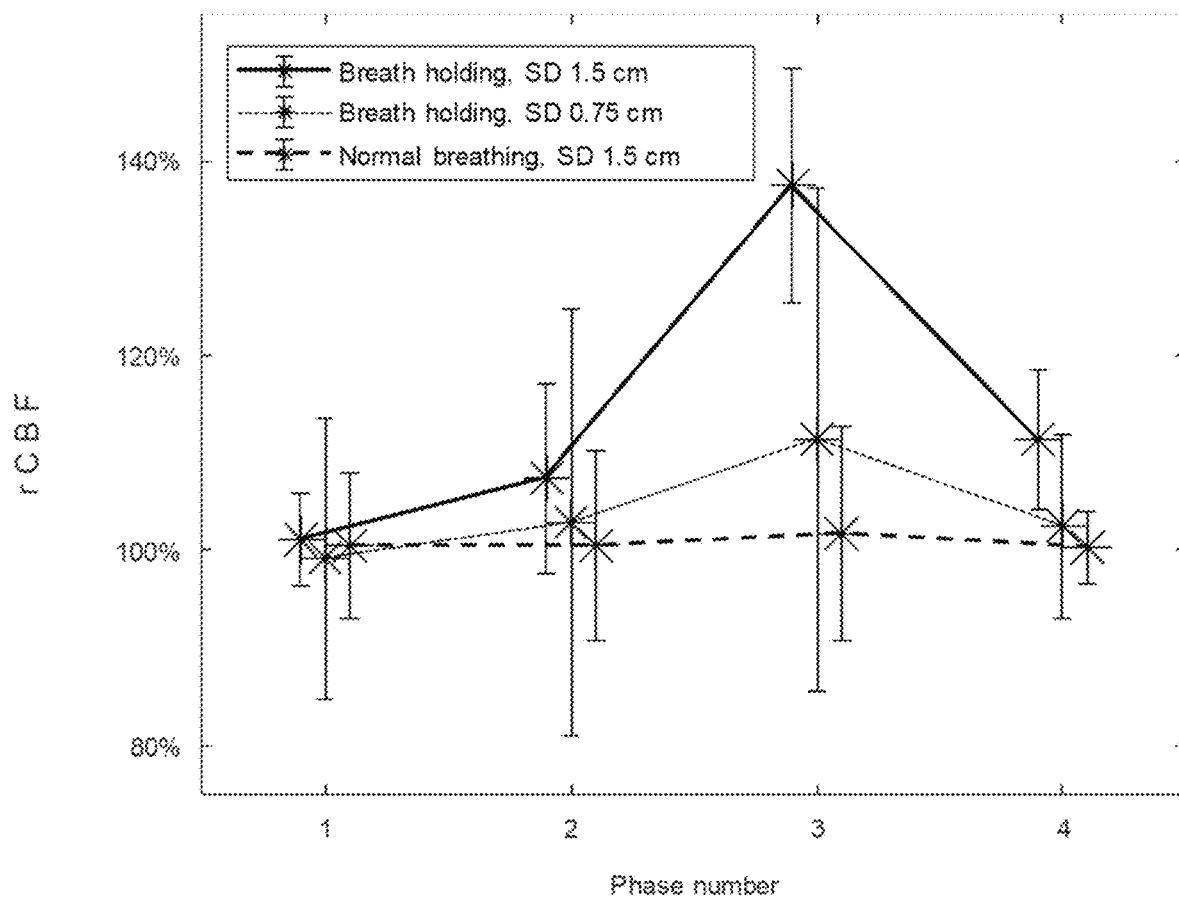
FIG. 32 is a graph of statistical analysis results of cerebral blood flow changes at different phases, according to an example.

To see the rCBF change due to the breath holding task, the mean values and standard deviations of rCBF during 2-4 s (Phase 1), 10-12 s (Phase 2, first several seconds of breath holding), 22-24 s (Phase 3, last several seconds of breath holding) and 37-39 s (Phase 4) were calculated and plotted, as shown in FIG. 32. The increase of rCBF values in Phase 3 at the S-D separation of 15 mm (case (i)) is clearly shown by the solid line in FIG. 32. In this case (S-D separation of 1.5 cm), some of light interacted with the cerebral blood flow. Blood flow change could be seen at an S-D separation larger than 1 cm as can be found in Selb, J., Boas, D. A., Chan, S.-T., Evans, K. C., Buckley, E. M., Carp, S. A., "Sensitivity of near-infrared spectroscopy and diffuse correlation spectroscopy to brain hemodynamics: simulations and experimental findings during hypercapnia," *Neurophotonics*. 1, 15005 488 (2014), which is hereby incorporated by reference in its entirety. The increase of rCBF values in Phase 3 at the S-D separation of 7.5 mm (case (iii)) was not as clear as that in case (i), as shown by the dotted line in FIG. 32. In this case (S-D separation of 0.75 cm), most of light interacted with the forehead skin rather than the brain, hence the breath holding task did not have the same significant impacts on the signal. The normal breathing measurements at the S-D separation of 1.5 cm (case (iii)) as a reference did not have significant change of rCBF, as shown by the dashed line in FIG. 32.

Modifications, additions, or omissions may be made to any of the above-described embodiments without departing from the scope of the disclosure. Any of the embodiments described above may include more, fewer, or other features without departing from the scope of the disclosure. Additionally, the steps of described features may be performed in any suitable order without departing from the scope of the disclosure. Also, one or more features from any embodiment may be combined with one or more features of any other embodiment without departing from the scope of the disclosure. The components of any embodiment may be integrated or separated according to particular needs without departing from the scope of the disclosure.

It should be understood that certain aspects described above can be implemented in the form of logic using computer software in a modular or integrated manner Based on the disclosure and teachings provided herein, a person of ordinary skill in the art will know and appreciate other ways and/or methods to implement the present invention using hardware and a combination of hardware and software.

Any of the software components or functions described in this application, may be implemented as software code using any suitable computer language and/or computational software such as, for example, Java, C, C#, C++ or Python, LabVIEW, Mathematica, or other suitable language/computational software, including low level code, including code written for field programmable gate arrays, for example in VHDL. The code may include software libraries for functions like data acquisition and control, motion control, image acquisition and display, etc. Some or all of the code may also run on a personal computer, single board computer, embedded controller, microcontroller, digital signal processor, field programmable gate array and/or any combination thereof or any similar computation device and/or logic device(s). The software code may be stored as a series of instructions, or commands on a CRM such as a random access memory (RAM), a read only memory (ROM), a magnetic medium such as a hard-drive or a floppy disk, or an optical medium such as a CD-ROM, or solid stage storage such as a solid state hard drive or removable flash memory device or any suitable storage device. Any such CRM may reside on or within a single computational apparatus, and may be present on or within different computational apparatuses within a system or network. Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

What is claimed is:

1. A method for interferometric speckle visibility spectroscopy, the method comprising:
   (i) recovering speckle field data or a speckle field pattern based at least in part on an off-axis interferogram recorded by one or more sensors over an exposure time; and
   (ii) determining at least one decorrelation time of a sample being analyzed based at least in part on speckle statistics of the speckle field data or the speckle field pattern.

2. The method of claim 1, further comprising determining a movement speed of one or more objects in the sample from the at least one decorrelation time.

3. The method of claim 1, wherein the exposure time is greater than the at least one decorrelation time.

4. The method of claim 1, further comprising:
   repeating (i) and (ii) for a plurality of off-axis interferograms; and
   determining a change between decorrelation times determined from the plurality of off-axis interferograms recorded at different exposure times.

5. The method of claim 1, wherein the at least one decorrelation time is determined based at least in part on one or more visibility factors, the one or more visibility factors determined based at least in part on the speckle statistics.

6. A method for interferometric speckle visibility spectroscopy, the method comprising:
   (i) recovering speckle field data based at least in part on an off-axis interferogram recorded by one or more sensors over an exposure time by:
      (a) Fourier transforming the off-axis interferogram to generate data in spatial frequency space comprising at least one off-axis lobe, and
      (b) using a spatial frequency filter to crop the speckle field data from the at least one off-axis lobe; and
   (ii) determining sample dynamics of a sample being analyzed based at least in part on speckle statistics of the speckle field data.

7. The method of claim 6, wherein (i) comprises shifting the cropped speckle field data to a central region of spatial frequency space.

8. The method of claim 6, wherein (i) comprises subtracting a reference interferogram from the off-axis interferogram.

9. The method of claim 8, wherein the reference interferogram has a uniform intensity.

10. The method of claim 6, wherein (i) and (ii) are repeated to determine sample dynamics for a plurality of off-axis interferograms.

11. The method of claim 10, wherein (ii) comprises determining a change between sample dynamics determined from two of the plurality of off-axis interferograms recorded at different exposure times.

12. The method of claim 6, wherein the sample dynamics comprise at least one decorrelation time.

13. A non-transitory computer readable media for interferometric speckle visibility spectroscopy, the non-transitory computer readable media comprising program instructions, wherein the program instructions, when read by one or more processors, cause the one or more processors to execute operations comprising:
   (i) recovering speckle field data or a speckle field pattern based at least in part on an off-axis interferogram recorded by one or more sensors over an exposure time; and
   (ii) determining at least one decorrelation time of a sample being analyzed based at least in part on speckle statistics of the speckle field data or the speckle field pattern.

14. The non-transitory computer readable media of claim 13, where the operations further comprise determining a movement of one or more objects in the sample from the at least one decorrelation time.

15. The non-transitory computer readable media of claim 13, wherein the exposure time is greater than the at least one decorrelation time.

16. The non-transitory computer readable media of claim 13, further comprising:
   repeating (i) and (ii) for a plurality of off-axis interferograms; and
   determining a change between decorrelation times determined from the plurality of off-axis interferograms recorded at different exposure times.

17. The non-transitory computer readable media of claim 13, wherein the at least one decorrelation time is determined based at least in part on one or more visibility factors, the one or more visibility factors determined based at least in part on the speckle statistics.

18. A non-transitory computer readable media for interferometric speckle visibility spectroscopy, the non-transitory computer readable media comprising program instructions, wherein the program instructions, when read by one or more processors, cause the one or more processors to execute operations comprising:
(i) recovering speckle field data based at least in part on an off-axis interferogram recorded by one or more sensors over an exposure time by:
   (a) Fourier transforming the off-axis interferogram to generate data in spatial frequency space comprising at least one off-axis lobe, and
   (b) using a spatial frequency filter to crop the speckle field data from the at least one off-axis lobe; and
(ii) determining sample dynamics of a sample being analyzed from speckle statistics of the speckle field data.

19. The non-transitory computer readable media of claim 18, wherein (i) comprises shifting the cropped speckle field data to a central region of spatial frequency space.

20. The non-transitory computer readable media of claim 18, wherein (i) comprises subtracting a reference interferogram from the off-axis interferogram.

21. The non-transitory computer readable media of claim 20, wherein the reference interferogram has a uniform intensity.

22. The non-transitory computer readable media of claim 18, wherein (i) and (ii) are repeated to determine sample dynamics for a plurality of off-axis interferograms.

23. The non-transitory computer readable media of claim 22, wherein (ii) comprises determining a change between sample dynamics determined from two of the plurality of off-axis interferograms recorded at different exposure times.

24. The non-transitory computer readable media of claim 18, wherein the sample dynamics comprise at least one decorrelation time.

25. An interferometric speckle visibility spectroscopy system, comprising:
one or more optical systems configured to interfere an off-axis reference beam with a sample signal; and
one or more processors configured to execute instructions to cause the one or more processors to:
(i) recover speckle field data based at least in part on an off-axis interferogram recorded by the one or more sensors over an exposure time, wherein the one or more processors are configured to:
   (a) Fourier transform the off-axis interferogram to generate data in spatial frequency space comprising at least one off-axis lobe, and
   (b) use a spatial frequency filter to crop speckle field data from the at least one off-axis lobe; and
(ii) determine sample dynamics of a sample being analyzed based at least in part on the cropped speckle field data.

* * * * *